(12) United States Patent
Stephanopoulos

(10) Patent No.: US 11,891,646 B2
(45) Date of Patent: Feb. 6, 2024

(54) BIOPROCESS AND MICROBE ENGINEERING FOR TOTAL CARBON UTILIZATION IN BIOFUEL PRODUCTION

(71) Applicant: Massachusetts Institute of Technology, Cambridge, MA (US)

(72) Inventor: Gregory Stephanopoulos, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 445 days.

(21) Appl. No.: 17/074,682

(22) Filed: Oct. 20, 2020

(65) Prior Publication Data

US 2021/0214756 A1 Jul. 15, 2021

Related U.S. Application Data

(62) Division of application No. 13/007,325, filed on Jan. 14, 2011, now abandoned.

(Continued)

(51) Int. Cl.
*C12P 7/649* (2022.01)
*C12P 7/6463* (2022.01)
(Continued)

(52) U.S. Cl.
CPC ............. *C12P 7/649* (2013.01); *C12M 23/58* (2013.01); *C12M 43/00* (2013.01); *C12P 7/10* (2013.01);
(Continued)

(58) Field of Classification Search
None
See application file for complete search history.

(56) References Cited

U.S. PATENT DOCUMENTS 3,910,826 A 10/1975 Kataoka
4,783,408 A 11/1988 Suzuki et al.
(Continued)

FOREIGN PATENT DOCUMENTS

DE 10059372 A1 6/2002
DE 10330375 A1 12/2004
(Continued)

OTHER PUBLICATIONS

[No author listed], DSM No. 10061. Retrieved on May 20, 2013 from http://www.dsmz.de/catalogues/details/culture/DSM-10061.html. 1 page.
(Continued)

*Primary Examiner* — William H. Beisner
(74) *Attorney, Agent, or Firm* — Wolf, Greenfield & Sacks, P.C.

(57) ABSTRACT

Some aspects of this invention provide methods and bioreactors for converting a carbon source into a lipid. In some embodiments, lipid production is carried out in an aerobic fermentor and carbon dioxide generated during lipid production is converted into a carbon substrate by $CO_2$ fixation in an anaerobic fermentor. In some embodiments, the carbon substrate generated by CO2 fixation is used as the carbon source for lipid production, thus achieving total carbon utilization in lipid production.

18 Claims, 6 Drawing Sheets

Related U.S. Application Data

(60) Provisional application No. 61/295,302, filed on Jan. 15, 2010.

(51) Int. Cl.
```
C12P 7/10      (2006.01)
C12P 7/54      (2006.01)
C12P 7/16      (2006.01)
C12M 1/00      (2006.01)
```

(52) U.S. Cl.
CPC .......... *C12P 7/16* (2013.01); *C12P 7/54* (2013.01); *C12P 7/6463* (2013.01); *Y02E 50/10* (2013.01); *Y02E 50/30* (2013.01)

(56) References Cited

U.S. PATENT DOCUMENTS

| | | | |
|---|---|---|---|
| 5,164,308 A * | 11/1992 | Kyle | A61K 51/1206 424/9.1 |
| 5,173,429 A | 12/1992 | Gaddy et al. | |
| 5,593,886 A | 1/1997 | Gaddy | |
| 5,807,722 A * | 9/1998 | Gaddy | C12M 29/04 435/163 |
| 6,136,577 A | 10/2000 | Gaddy | |
| 6,340,581 B1 | 1/2002 | Gaddy | |
| 6,368,819 B1 | 4/2002 | Gaddy et al. | |
| 7,704,723 B2 | 4/2010 | Huhnke et al. | |
| 2007/0004016 A1 | 1/2007 | Picataggio et al. | |
| 2007/0048848 A1 | 3/2007 | Sears | |
| 2007/0275447 A1 | 11/2007 | Lewis et al. | |
| 2009/0004715 A1 | 1/2009 | Coragliotti et al. | |
| 2009/0317882 A1 | 12/2009 | Cheng et al. | |
| 2011/0177564 A1 | 7/2011 | Stephanopoulos | |
| 2011/0223641 A1 | 9/2011 | Stephanopoulos et al. | |

FOREIGN PATENT DOCUMENTS

| | | |
|---|---|---|
| DE | 102006047339 A1 | 4/2008 |
| JP | 50005581 A | 1/1975 |
| RU | 2080388 C1 | 5/1997 |
| WO | WO 1998/000558 A1 | 1/1998 |
| WO | WO 2000/068407 A1 | 11/2000 |
| WO | WO 2002/008438 A2 | 1/2002 |
| WO | WO 2007/117157 A1 | 10/2007 |
| WO | WO 2008/115080 A1 | 9/2008 |
| WO | WO 2009/064200 A2 | 5/2009 |
| WO | WO 2007/073552 A1 | 6/2009 |
| WO | WO 2009/105372 A1 | 8/2009 |
| WO | WO 2009/133351 A2 | 11/2009 |

OTHER PUBLICATIONS

[No author listed], DSM No. 43535. Retrieved on May 20, 2013 from http://www.dsmz.de/catalogues/details/culture/DSM-43535.html. 1 page.

Database WPI. Accession No. 1975-41763W. English abstract for JP 50 005581 A. Jan. 21, 1975.

Agrawal et al., Sustainable fuel for the transportation sector. Proc Natl Acad Sci U S A. Mar. 20, 2007;104(12):4828-33. Epub Mar. 14, 2007.

Alvarez et al., Triacylglycerols in prokaryotic microorganisms. Appl Microbiol Biotechnol. Dec. 2002;60(4):367-76. Epub Oct. 12, 2002.

Balan et al., Lignocellulosic biomass pretreatment using AFEX. Biofuels: Methods and protocols, Methods Mol Biol. Ed. Mielenz. Humana Press. 2009;581(Chapter 5):61-77. doi: 10.1007/978-1-60761-214-8_5.

Balch et al., Acetobacterium, a new genus of hydrogen-oxidizing, carbon dioxide-reducing, anaerobic bacteria. Int J Syst Bacteriol. Oct. 1977;27(4):355-61.

Beopoulos et al., Yarrowia lipolytica as a model for bio-oil production. Prog Lipid Res. Nov. 2009;48(6):375-87. doi: 10.1016/j.plipres.2009.08.005. Epub Aug. 29, 2009.

Chen et al., Screening of oleaginous yeast strains tolerant to lignocellulose degradation compounds. Appl Biochem Biotechnol. Dec. 2009;159(3):591-604. Epub Jan. 21, 2009.

Dong et al., In situ carbon dioxide fixation in the process of natural astaxanthin production by a mixed culture of Haematococcus pluvialis and Phaffia rhodozyma. Catalysis Today. Dec. 2004;98:537-544.

Drake et al., Old acetogens, new light. Ann N Y Acad Sci. Mar. 2008;1125:100-28. doi: 10.1196/annals.1419.016. Epub Mar. 26, 2008.

El Abed et al., Microalgae: a potential source of polyunsaturated fatty acids. Nutr Health. 2008;19(3):221-6.

Gouveia et al., Microalgae as a raw material for biofuels production. J Ind Microbiol Biotechnol. Feb. 2009;36(2):269-74. doi:10.1007/s10295-008-0495-6. Epub Nov. 4, 2008.

Greenwell et al., Placing microalgae on the biofuels priority list: a review of the technological challenges. J Royal Soc Interface. May 6, 2010;7(46):703-26. Epub Dec. 23, 2009.

Gregory et al., Graphite electrodes as electron donors for anaerobic respiration. Environ Microbiol. Jun. 2004;6(6):596-604. doi: 10.1111/j.1462-2920.2004.00593.x.

He et al., Application of bacterial biocathodes in microbial fuel cells. Electroanalysis. Oct. 2006;18(19-20):2009-2015.

Kerscher et al., The complete mitochondrial genome of yarrowia lipolytica. Comp Funct Genomics. 2001;2(2):80-90. doi: 10.1002/cfg.72.

Li et al., Partial characterization of a cDNA for human stearoyl-CoA desaturase and changes in its mRNA expression in some normal and malignant tissues. Int J Cancer. May 1, 1994;57(3):348-52.

Li et al., Perspectives of microbial oils for biodiesel production. Appl Microbiol Biotechnol. Oct. 2008;80(5):749-56. doi: 10.1007/s00253-008-1625-9. Epub Aug. 9, 2008.

Lu et al., Overproduction of free fatty acids in *E. coli*: implications for biodiesel production. Metab Eng. Nov. 2008;10(6):333-9. doi:10.1016/j.ymben.2008.08.006. Epub Sep. 9, 2008.

Martin et al., Regulation of long chain unsaturated fatty acid synthesis in yeast. Biochim Biophys Acta. Mar. 2007; 1771(3):271-85. Epub Jul. 13, 2006.

Papanikolaou et al., Single cell oil production by Yarrowia lipolytica growing on an industrial derivative of animal fat in batch cultures. Appl Microbiol Biotechnol. Mar. 2002;58(3):308-12. Epub Dec. 11, 2001.

Ratledge, Microbial routes to lipids. Biochem Soc Trans. Dec. 1989;17(6):1139-41.

Sokolova et al., Laser-induced liquid bead ion desorption-MS of protein complexes from blue-native gels, a sensitive top-down proteomic approach. Proteomics. Apr. 2010;10(7):1401-7. doi: 10.1002/pmic.200900756. Epub Feb. 1, 2010.

Steen et al., Microbial production of fatty-acid-derived fuels and chemicals from plant biomass. Nature. Jan. 28, 2010;463(7280):559-62. doi: 10.1038/nature08721.

Stukey et al., The OLE1 gene of *Saccharomyces cerevisiae* encodes the delta 9 fatty acid desaturase and can be functionally replaced by the rat stearoyl-CoA desaturase gene. J Biol Chem. Nov. 25, 1990;265(33):20144-9.

Voss et al., High cell density cultivation of Rhodococcus opacus for lipid production at a pilot-plant scale. Appl Microbiol Biotechnol. May 2001;55(5):547-55. Epub Apr. 10, 2001.

White et al., Quantitative population dynamics of microbial communities in plankton-fed microbial fuel cells. ISME J. Jun. 2009;3(6):635-46. doi: 10.1038/ismej.2009.12. Epub Feb. 26, 2009.

Yang et al., Dilute acid and autohydrolysis pretreatment. Biofuels: Methods and protocols, Methods in Mol Biol. Ed. Mielenz. Humana Press. 2009;581(Chapter 8):103-14. doi: 10.1007/978-1-60761-214-8_8.

Zhang et al., Human stearoyl-CoA desaturase: alternative transcripts generated from a single gene by usage of tandem polyadenylation sites. Biochem J. May 15, 1999;340 ( Pt 1 ):255-64.

* cited by examiner

BIOPROCESS AND MICROBE ENGINEERING FOR TOTAL CARBON UTILIZATION IN BIOFUEL PRODUCTION

RELATED APPLICATIONS

This application is a divisional of U.S. patent application Ser. No. 13/007,325, filed Jan. 14, 2011, which claims priority under 35 U.S.C. § 119(e) to U.S. provisional patent application Ser. No. 61/295,302, filed Jan. 15, 2010, the entire contents of each of which are incorporated herein by reference.

GOVERNMENT SUPPORT

This invention was made with Government support under Grant No. DE-AR0000059 awarded by the Department of Energy. The Government has certain rights in the invention.

BACKGROUND

The main limitation in biodiesel production is the availability of oil feedstock that is both expensive and in short supply. Furthermore, yields of oil from oil seeds and vegetable oil feedstocks (in gallons of gasoline equivalent per hectare and year) are very low, approximately ⅕-¹⁄₁₀ of the corresponding yields of carbohydrate energy crops (1). Hence, conversion of carbohydrate feedstocks to lipids and oils has attracted considerable attention in recent years.

Production of oil by microbes, also referred to as microbial oil or Single Cell Oil (SCO), has primarily been targeted for human consumption and mostly restricted to commercial production of dietary supplements, such as edible polyunsaturated fatty acids (PUFA) (2). The cost-effective use of microbial oil for biofuel applications, especially as feedstock in biodiesel production, requires several considerations such as, optimizing oil quality and oil properties, ability to assimilate various carbon sources, high final oil concentrations and, most importantly, high yields, defined as actual grams of oil produced per gram of carbohydrate substrate consumed. The importance of yield as defining factor in economical biodiesel production stems from the large contribution of the feedstock cost to the total biofuel manufacturing cost (upwards of 55% by most estimates). Many microbes are known to produce oil such as bacteria, yeast and algae with sub-optimal oil yields (3). The low oil yield (along with low volumetric productivity) is a central reason that microbial-derived oil has failed to break commercial scale.

Several attempts have been made to produce oil using bacterial species and yeasts. Examples include the oleaginous bacterium *Rhodococcus opacus* (4) that achieved a yield close to 10% which is one third of the maximum yield possible making the process uneconomical (5). Recently, *E. coli* was genetically engineered to directly secrete free fatty acids (6) or fatty acid methyl esters (FAME/biodiesel) directly in the extracellular medium (7), at oil conversion yields between 4.8% and 13%, compared to a maximum theoretical yield of 30-33%. Similarly, oleaginous yeasts, such as *Yarrowia lipolytica*, are being genetically modified for bio-oil production (8). Current oil production using oleaginous yeasts stands at 4-6 grams of oil per liter (9), which is considered very low for commercial application.

In notable contrast to the low land-based productivity of vegetable oil mentioned above is the use of microalgae for oil production by direct photosynthetic fixation of atmospheric carbon dioxide. The broad distribution of algal cultivation along with lack of competition for food-producing cropland makes algal-derived oils a compelling proposition (10), assuming that a number of fundamental limitations will be satisfactorily resolved first (11). These include the possibility that algal cultures may be out-competed in open systems due to their slow growth rate relative to other species, and very low algal and oil concentrations, which makes dewatering and biomass processing extremely expensive.

SUMMARY

The conversion of carbohydrates to carbon substrates useful for biofuel production (e.g., ethanol or triacylglycerides) in living cells is an inefficient process. For example, approximately half of the glucose feedstock in an ethanol fermentation process is lost as $CO_2$. This is the result of carbon oxidation that is necessary to generate the reducing equivalents required to lower the oxygen content of an initial glucose molecule ($C_6H_{12}O_6$) to that of the more reduced product ethanol ($C_2H_6O$). This picture does not differ significantly in other types of biofuels (e.g., butanol, lipids and oils) produced from sugars such as glucose or xylose, products themselves of either starch or cellulosic/hemicellulosic biomass hydrolysis.

If the emitted $CO_2$ could be captured, for example, by using hydrogen from a non-fossil fuel source, the amount of land required to produce a given amount of biofuel would be reduced by two thirds (1). While thermochemical processes were contemplated in the above $CO_2$ fixation concept, aspects of this invention provide biological methods to achieve fixation of $CO_2$, which have a higher overall yield as they operate closer to equilibrium and are consequently more efficient. The use of the biological methods for $CO_2$ fixation provided herein is useful to increase dramatically the amount of liquid fuels that can be obtained from a certain land area. Additionally, some of these methods provide an excellent means for hydrogen storage.

Some aspects of this invention provide methods, microorganisms, and bioreactors for the generation of TAG from a carbon source, in which $CO_2$ generated during TAG production from the carbon source is used in a biological $CO_2$ fixation process yielding a carbon substrate. Some aspects of this invention provide methods, microorganisms, and bioreactors for heterotrophic triacylglycerol (TAG) production from a carbon substrate that is a product of biological $CO_2$ fixation, for example, by anaerobic, $CO_2$ fixing organisms that utilize as reductant either gaseous hydrogen or electrons provided by a biocathode. Some aspects of this invention provide methods, microorganisms, and bioreactors for the aerobic generation of TAG from a carbon substrate generated by anaerobic $CO_2$ fixation, wherein $CO_2$ generated during conversion of the carbon substrate is used in the anaerobic $CO_2$ fixation.

Biological $CO_2$ fixation requires the concerted action of various dehydrogenases (among other pathway enzymes), which are typically obligate anaerobic enzymes. TAG production, on the other hand, is an energy intensive process requiring the oxidation of substantial amounts of carbon for the production of the energy and reducing equivalents embodied in the production of TAG, the most energy dense compound in nature. This should be, optimally, an aerobic process, as the required amounts of energy for oil production would be prohibitively slow to produce under anaerobic conditions by substrate-level phosphorylation. The above conflicting requirements suggest that it would be highly unlikely to achieve both $CO_2$ reduction and TAG production in the same cellular environment.

Some aspects of this invention provide a solution to this problem in separating the aerobic and anaerobic functions into two different bioreactors: one for the intensely aerobic production of TAG (e.g., oil) and the other for the anaerobic reduction of $CO_2$ in the presence of hydrogen or electric current. In some embodiments, an oleaginous microbe optimized for TAG production from a specific carbon substrate (e.g., carbohydrate feedstock) is employed in the methods and bioreactors provided herein for the aerobic conversion of a carbon source to TAG. In some embodiments, non-photosynthetic, anaerobic $CO_2$ fixation is achieved through the use of bacteria, for example, acetogenic bacteria. In some embodiments, the bacteria are genetically modified, or pathway-engineered. In some embodiments, the bacteria are *Clostridia*. In some embodiments, $CO_2$ fixation is achieved through the use of *Clostridia* under anaerobic culture conditions. In some embodiments, $CO_2$ fixation is achieved through direct electron transfer from the biocathode of a reverse microbial fuel cell (MFC).

Some aspects of this invention provide a method comprising (a) culturing a first organism in the presence of a carbon source under conditions suitable for the organism to oxidize the carbon source, wherein the organism produces $CO_2$ as part of the oxidation process; and (b) culturing a second organism in the presence of $CO_2$ produced in (a) under conditions suitable for the second organism to reduce the $CO_2$, wherein the organism produces a carbon substrate as part of the reduction process. In some embodiments, the conditions of (a) are oxidizing conditions. In some embodiments, the conditions of (a) are aerobic conditions. In some embodiments, the conditions of (b) are reducing conditions. In some embodiments, the conditions of (b) are anaerobic conditions. In some embodiments, the culturing of (a) and/or (b) is carried out in a fermentor. In some embodiments, the culturing of (a) and of (b) is carried out in separate fermentors. In some embodiments, the culturing of (a) is carried out in an aerobic fermentor. In some embodiments, the culturing of (b) is carried out in an anaerobic fermentor. In some embodiments, the method further comprises contacting the first organism with an oxidizing agent. In some embodiments, the oxidizing agent is $O_2$. In some embodiments, the method further comprises contacting the second organism with a reducing agent. In some embodiments, the reducing agent is $H_2$, CO, syngas, or $H_2S$. In some embodiments, the $O_2$ and/or the $H_2$ are generated by electrolysis of $H_2O$. In some embodiments, the syngas is generated from coal or natural gas. In some embodiments, the culturing of (a) and/or (b) is carried out in a liquid medium. In some embodiments, $O_2$ is dispersed in the liquid medium of the aerobic fermentor in the form of micro-bubbles; and/or $H_2$ is dispersed in the liquid medium of the anaerobic fermentor in the form of micro-bubbles. In some embodiments, the method further comprises providing electrons to the organism of (b) by contacting the organism of (b) with an electric current. In some embodiments, the electric current is provided via one or more electrodes. In some embodiments, the carbon source is a carbohydrate. In some embodiments, the carbohydrate is glucose, fructose, ethanol, butanol, acetic acid, biomass, cellulose, or hemicellulose. In some embodiments, a product of the carbon source oxidization process in (a) is a biofuel. In some embodiments, the product of the carbon source oxidization process in (a) is a lipid. In some embodiments, the product of the carbon source oxidization is an edible lipid, or a precursor thereof. In some embodiments, the carbon substrate produced in (b) is a biofuel. In some embodiments, the carbon substrate produced in (b) is ethanol. In some embodiments, the carbon substrate produced in (b) is a carbon source that can be oxidized by the organism of (a). In some embodiments, the carbon substrate produced in (b) is acetic acid or acetate, biomass, cellulose, or hemi-cellulose. In some embodiments, the carbon substrate produced in (b) is processed for use as a carbon source in (a). In some embodiments, the processing comprises hydrolysis of at least part of the carbon substrate. In some embodiments, the carbon source of (a) comprises at least part of the carbon substrate produced in (b). In some embodiments, the carbon source of (a) comprises the carbon substrate produced in (b). In some embodiments, the carbon source of (a) consists of the carbon substrate produced in (b). In some embodiments, the organism of (a) is a microorganism. In some embodiments, the organism of (b) is a microorganism. In some embodiments, the organism of (a) is an oleaginous yeast. In some embodiments, the organism of (a) is *Y. lipolytica*. In some embodiments, the organism of (b) is a $CO_2$-fixing bacterium. In some embodiments, the organism of (b) is an acetogenic bacterium. In some embodiments, the organism of (b) is a *Clostridium* sp. *bacterium*. In some embodiments, the organism of (b) is *C. acetobutylicum, C. ljungdahlii, C. carboxydivorans*, or *C. autoethanogenum, C. thermohydrosulfuricum, C. thermocellum*, or *C. thermoanaerofacter ethanoliticus*, or any other CO2 fixing microorganism descried herein. In some embodiments, the organism of (a) and/or (b) is genetically modified. In some embodiments, the organism of (a) overexpresses an SCD gene or comprises any genetic modification described herein for TAG-producing organisms, for example, in Example 1. In some embodiments, the organism of (b) comprises a genetic modification that increases the activity of a Wood-Ljungdahl metabolic pathway member in the organism, or any modification described for $CO_2$ fixing organisms herein.

Some aspects of this invention provide a bioreactor comprising (a) an aerobic fermentor comprising (i) a carbon source, (ii) an organism oxidizing the carbon source and generating $CO_2$, and (iii) an outflow, through which the $CO_2$ is removed from the fermentor; and (b) an anaerobic fermentor comprising (i) an organism reducing $CO_2$, and (ii) an inflow providing $CO_2$ to the fermentor, wherein the inflow is connected to the outflow of the aerobic fermentor in (a)(iii). In some embodiments, the aerobic and/or the anaerobic fermentor comprises a liquid medium. In some embodiments, the aerobic fermentor comprises an oxidizing agent and/or the anaerobic fermentor comprises a reducing agent. In some embodiments, the oxidizing agent is $O_2$ and/or the reducing agent is $H_2$, CO, syngas, or $H_2S$. In some embodiments, the bioreactor further comprises an electrolysis apparatus that generates $O_2$ and $H_2$ from $H_2O$, wherein the $O_2$ is delivered to the aerobic fermentor and/or the $H_2$ is delivered to the anaerobic fermentor. In some embodiments, the aerobic fermentor comprises $O_2$ in the form of microbubbles and/or wherein the anaerobic fermentor comprises $H_2$ in the form of micro-bubbles. In some embodiments, the anaerobic fermentor comprises one or more electrodes delivering an electric current to the fermentor in an amount sufficient to provide the organism in the anaerobic fermentor with electrons for $CO_2$. In some embodiments, the carbon source is glucose, glucose, fructose, ethanol, butanol, acetic acid or acetate, biomass, cellulose, or hemicellulose. In some embodiments, a product of oxidizing the carbon source is a biofuel. In some embodiments, a product of oxidizing the carbon source is a lipid. In some embodiments, the lipid is an edible lipid or a precursor thereof. In some embodiments, the lipid is a triacylglyceride (TAG). In some embodiments, the aerobic fermentor further comprises an outflow through which the product of oxidizing the carbon source is removed. In some embodiments, the inflow of (b)(ii) is further connected to an external source of $CO_2$. In some embodiments, a product of $CO_2$ reduction in the anaerobic fermentor is a carbon source that can be oxidized by the organism in the aerobic fermentor. In some embodiments, a product of $CO_2$ reduction in the anaerobic fermentor is biomass, cellulose, or hemi-cellulose. In some embodiments, a product of $CO_2$ reduction is a biofuel. In some embodiments, a product of $CO_2$ reduction is ethanol or butanol. In some embodiments, a product of $CO_2$ reduction is acetic acid or acetate. In some embodiments, the anaerobic fermentor comprises an outflow through which a product of $CO_2$ reduction is removed. In some embodiments, the outflow through which the product of $CO_2$ reduction is removed from the anaerobic fermentor is connected to the aerobic fermentor and the product of $CO_2$ reduction in the anaerobic fermentor is delivered to the aerobic fermentor. In some embodiments, the product of $CO_2$ reduction in the anaerobic fermentor constitutes at least part of the carbon source in the aerobic fermentor. In some embodiments, the product of $CO_2$ reduction in the anaerobic fermentor constitutes the carbon source in the aerobic fermentor. In some embodiments, the influx of carbon into the bioreactor is limited to the influx of $CO_2$ into the anaerobic fermentor. In some embodiments, the organism of (a) is a microorganism. In some embodiments, the organism of (b) is a microorganism. In some embodiments, the organism of (a) is an oleaginous yeast. In some embodiments, the organism of (a) is *Y. lipolytica*. In some embodiments, the organism of (b) is a $CO_2$-fixing bacterium. In some embodiments, the organism of (b) is an acetogenic bacterium. In some embodiments, the organism of (b) is a *Clostridium* sp. *bacterium*. In some embodiments, the organism of (b) is *C. acetobutylicum, C. ljungdahlii, C. carboxydivorans, C. autoethanogenum, C. thermohydrosulfuricum, C. thermocellum*, or *C. thermoanaerofacter ethanoliticus*. In some embodiments, the organism of (a) and/or (b) is genetically modified. In some embodiments, the organism of (a) overexpresses an SCD gene or comprises any genetic modification described herein for TAG-producing organisms, for example, in Example 1. In some embodiments, the organism of (b) comprises a genetic modification that increases the activity of a Wood-Ljungdahl metabolic pathway member in the organism, or any modification described for $CO_2$ fixing organisms herein.

Other advantages, features, and uses of the invention will be apparent from the detailed description of certain non-limiting embodiments, the drawings, which are schematic and not intended to be drawn to scale, and the claims.

DEFINITIONS

Figure 1:
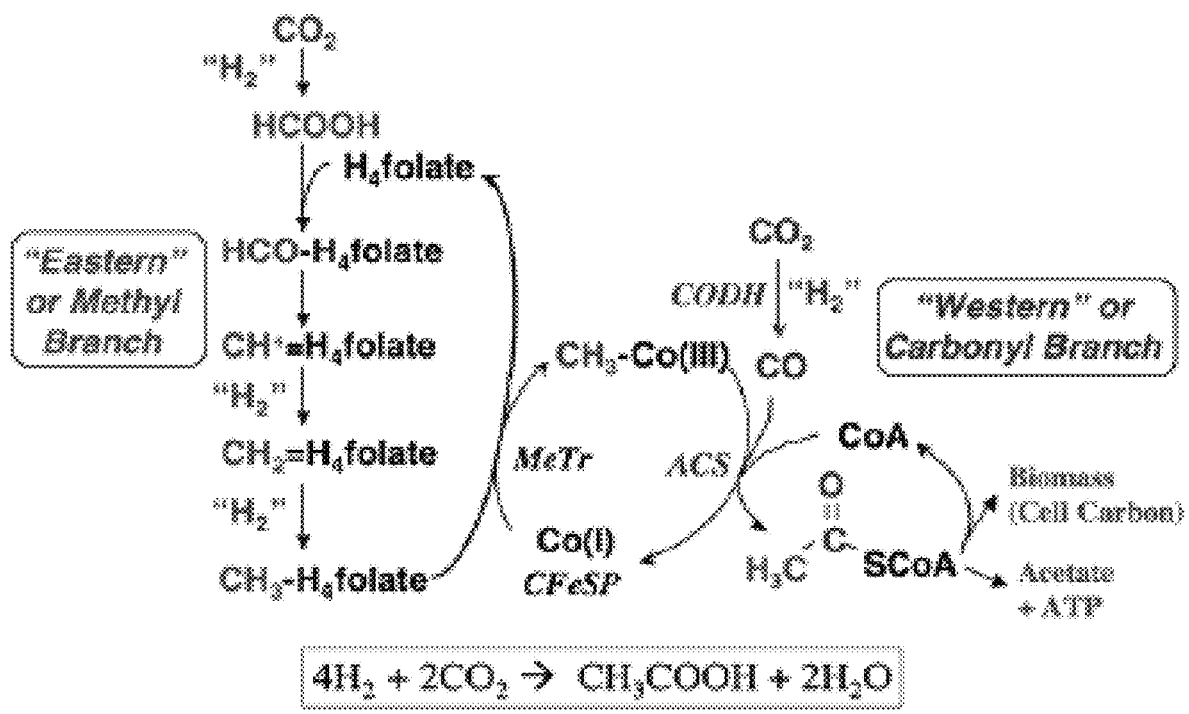
FIG. 1. The Wood-Ljungdahl pathway. "$H_2$" is used in a very general sense to designate the requirement for two electrons and two protons in the reaction.

The term "acetogen" or "acetogenic microbe" or "acetogenic bacterium" is art-recognized and refers to a microorganism that generates acetate as a product of anaerobic $CO_2$ fixation. Acetogens are found in a variety of anaerobic habitats and can use a variety of compounds as sources of energy and carbon; the best studied form of acetogenic metabolism involves the use of carbon dioxide as a carbon source and hydrogen as an energy source.

The term "aerobic conditions" is art recognized and refers to conditions that provide sufficient oxygen for efficient oxidation of a carbon source by an aerobic organism. In some embodiments, aerobic conditions are conditions that provide an abundance or even an overabundance of oxygen, for example, in the form of micro-bubbles of oxygen in a liquid medium. For example, a fermentor comprising a gaseous phase comprising at least 10%, at least 15%, at least 20%, at least 30%, at least 50%, or more oxygen is referred to as an aerobic fermentor.

The term "anaerobic conditions" is art recognized and refers to conditions that do not provide sufficient oxygen for efficient carbon oxidation by an aerobic organism. In some embodiments, anaerobic conditions are characterized by the essential absence of oxygen. In other embodiments, the oxygen content is less than required by a microbe employed to efficiently oxidate a carbon source. For example, a fermentor comprising a liquid medium and a gaseous phase comprising less than 5%, less than 2%, less than 1%, less than 0.5%, less than 0.1%, less than 0.01%, or less than 0.001% oxygen is referred to as an anaerobic fermentor.

The term "biofuel" refers to a fuel that is derived from a biological source, such as a living cell, microbe, fungus, or plant. The term includes fuel directly obtained from a biological source, for example, by conventional extraction, distillation, or refining methods, and fuel produced by processing a biofuel precursor obtained from a biological source, for example by chemical modification, such as transesterification procedures. Examples of biofuels that are directly obtainable are alcohols such as ethanol, propanol, and butanol, fat, and oil. Examples of biofuels that are obtained by processing of a biofuel precursor (e.g., a lipid, such as a TAG), are biodiesel (e.g., produced by transesterification of a lipid), and green diesel/modified oil fuels (e.g., produced by hydrogenation of an oil). Biodiesel, also referred to as fatty acid methyl (or ethyl) ester, is one of the economically most important biofuels today and can be produced on an industrial scale by transesterification of lipids, in which sodium hydroxide and methanol (or ethanol) reacts with a lipid, for example, a triacylglycerol, to produce biodiesel and glycerol.

The term "biomass" refers to material produced by growth and/or propagation of a living cell or organism, for example, a microbe. Biomass may contain cells, microbes, plants, and/or intracellular contents, for example cellular fatty acids and TAGs, as well as extracellular material. Extracellular material includes, but is not limited to, compounds secreted by a cell, for example, secreted fatty acids or TAGs. In some embodiments, biomass is processed before being used as a carbon source for aerobic biofuel production. For example, biomass comprising a high content of non-fermentable carbohydrates, such as cellulose, can be hydrolyzed into fermentable carbohydrates by methods known to those of skill in the art. In some embodiments, the pretreatment of biomass feedstock includes depolymerizing cellulose and/or hemicellulose components to monomeric sugars using a pretreatment method known to those of skill in the art, for example, a dilute acid or ammonia fiber expansion (AFEX) method (see, e.g., Yang B, Wyman C E. *Dilute acid and autohydrolysis pretreatment.* Methods Mol Biol. 2009; 581:103-14; Balan V, Bals B, Chundawat S P, Marshall D, Dale B E, *Lignocellulosic biomass pretreatment using AFEX Methods* Mol Biol. 2009; 581:61-77). Other methods for depolymerization of biomass polymers to monomeric sugars are well known to those of skill in the art and are contemplated to be used in some embodiments of this invention.

The term "culturing" refers to maintaining a culture of an organism, for example, a microbe described herein for a period of time, generally, for a period of time sufficient for a desired fermentation process to be carried out by the microbe. In some embodiments, the culture comprises a microbe described herein and a medium, for example, a liquid medium. In some embodiments, the culture comprises a carbon source, for example a carbon source dissolved in the culture medium. For example, in some embodiments, a microbe is cultured in an aerobic fermentor in a liquid medium in the presence of a carbon source (e.g., acetate, or a soluble sugar) dissolved in the medium. In some embodiments, the culture comprises a salt and/or buffer establishing conditions of salinity, osmolarity, and pH, that are amenable to survival, growth, and/or conversion of the carbon source to a biofuel or biofuel precursor by the cultured organism. In some embodiments, the culture comprises an additional component, for example, an additive. Non-limiting examples of additives are nutrients, enzymes, amino acids, albumin, growth factors, enzyme inhibitors (for example protease inhibitors), fatty acids, lipids, hormones (e.g., dexamethasone and gibberellic acid), trace elements, inorganic compounds (e.g., reducing agents, such as manganese), redox-regulators (e.g., antioxidants), stabilizing agents (e.g., dimethylsulfoxide), polyethylene glycol, polyvinylpyrrolidone (PVP), gelatin, antibiotics (e.g., Brefeldin A), salts (e.g., NaCl), chelating agents (e.g., EDTA, EGTA), and enzymes (e.g., cellulase, dispase, hyaluronidase, or DNase). In some embodiments, the culture may comprise a compound, for example, a small molecule compound or drug, inducing or inhibiting transcription from a conditional or inducible promoter, for example doxicycline, tetracycline, tamoxifen, IPTG, hormones, or metal ions. While the specific culture conditions, for example, the concentration of the carbon source, will depend upon the respective engineered microorganism to be cultured, general methods and culture conditions for the generation of microbial cultures are well known to those of skill in the art, and are described, for example, in J. Sambrook and D. Russell, *Molecular Cloning: A Laboratory Manual*, Cold Spring Harbor Laboratory Press; 3rd edition (Jan. 15, 2001); David C. Amberg, Daniel J. Burke; and Jeffrey N. Strathern, *Methods in Yeast Genetics: A Cold Spring Harbor Laboratory Course Manual*, Cold Spring Harbor Laboratory Press (April 2005); John N. Abelson, Melvin I. Simon, Christine Guthrie, and Gerald R. Fink, *Guide to Yeast Genetics and Molecular Biology, Part A, Volume* 194 (Methods in Enzymology Series, 194), Academic Press (Mar. 11, 2004); Christine Guthrie and Gerald R. Fink, *Guide to Yeast Genetics and Molecular and Cell Biology, Part B, Volume* 350 (Methods in Enzymology, Vol 350), Academic Press; 1st edition (Jul. 2, 2002); and Christine Guthrie and Gerald R. Fink, *Guide to Yeast Genetics and Molecular and Cell Biology, Part C, Volume* 351, Academic Press; 1st edition (Jul. 9, 2002), all of which are incorporated by reference herein.

The term "fermentor" refers to an enclosure, or partial enclosure, in which a biological and/or chemical reaction takes place, at least part of which involves a living organism or part of a living organism. Where liquid cultures are used for fermentation, the fermentor is typically a culture vessel able to hold the desired amount of liquid media. If a gaseous phase is employed in the fermentation process, the fermentor employed will have a volume allowing accommodation of the gaseous phase and, if the gaseous phase is not air, the fermentor is typically sealed in an airtight manner. Typically, a fermentor comprises one or more inflows and/or outflows for the introduction and/or removal of liquids, solids, and/or gas into and/or out of the fermentor. Suitable fermentor configurations will be apparent to those of skill in the art. For example, in some embodiments, a continuous stirred tank reactor (CTSR), a bubble column reactor (BCR) or a trickle bed reactor (TBR), may be employed. In some embodiments, a fermentor comprises a culture of microbes performing the fermentation process. In some embodiments, a fermentor may continuously or semi-continuously be fed with new microbes from a growth or culture vessel. Depending on the fermentation scale, fermentors can range from volumes of milliliters to thousands of liters or more. Some fermentors according to aspects of this invention may include cell cultures where microbes are in contact with moving liquids and/or gas bubbles. Microbes or microbe cultures in accordance with aspects of this invention may be grown in suspension or attached to solid phase carriers. Non-limiting examples of carrier systems include microcarriers (e.g., polymer spheres, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. Carriers can be fabricated from materials such as dextran, gelatin, glass, and cellulose.

The term "lipid" refers to fatty acids and their derivatives. Accordingly, examples of lipids include fatty acids (FA, both saturated and unsaturated); glycerides or glycerolipids, also referred to as acylglycerols (such as monoglycerides (monoacylglycerols), diglycerides (diacylglycerols), triglycerides (triacylglycerols, TAGs, or neutral fats); phosphoglycerides (glycerophospholipids); nonglycerides (sphingolipids, sterol lipids, including cholesterol and steroid hormones, prenol lipids including terpenoids, fatty alcohols, waxes, and polyketides); and complex lipid derivatives (sugar-linked lipids or glycolipids, and protein-linked lipids). Lipids are an essential part of the plasma membrane of living cells and microbes. Some cells and microbes also produce lipids to store energy, for example in the form of triacylglycerols in lipid droplets.

The term "syngas" is art recognized and refers to a gas mixture that contains varying amounts of carbon monoxide and hydrogen, and frequently also carbon dioxide. Syngas can be produced from coal, first by pyrolysis to coke (destructive distillation), followed by alternating blasts of steam and air, or from biomass or municipal waste. Syngas can also be produced by steam reforming of natural gas or liquid hydrocarbons. In some embodiments, syngas is introduced into the anaerobic fermentor to provide reductants (CO and $H_2$) and, in some cases, also $CO_2$ for fixation by a $CO_2$ fixing organism. In some embodiments, natural gas or coal is used to produce syngas, which is then used according to aspects of this invention to produce a lipid, for example a TAG. In some embodiments, the TAG is a biofuel. In some embodiments, the TAG is an edible lipid or a precursor of an edible lipid. Accordingly, some aspects of this invention provide methods to convert an inorganic carbon source (e.g., coal or natural gas) into a biofuel or an edible lipid, for example, via syngas distillation and biological fermentation steps as described herein The term "triacylglyceride" (TAG, sometimes also referred to as triacylglycerol or triglyceride) refers to a molecule comprising a single molecule of glycerol covalently bound to three fatty acid molecules, aliphatic monocarboxylic acids, via ester bonds, one on each of the glycerol molecule's three hydroxyl (OH) groups. Triacylglycerols are highly concentrated stores of metabolic energy because of their reduced, anhydrous nature, and are a suitable feedstock for biodiesel production.

DETAILED DESCRIPTION

Some aspects of this invention provide novel bioprocessing methods, microorganisms, and bioreactors for the production of lipids, for example, of TAGs. Some aspects of this invention provide methods and bioreactors in which $CO_2$ generated during the aerobic conversion of a carbon source to lipid (e.g., TAG), for example, in an aerobic fermentor, is used in an anaerobic $CO_2$ fixation process yielding a carbon substrate, for example, in a separate, anaerobic fermentor. In some embodiments, the carbon substrate produced by anaerobic $CO_2$ fixation is itself a biofuel, for example, ethanol. In some embodiments, the carbon substrate produced by anaerobic $CO_2$ fixation is a compound that can be used as the carbon source for the aerobic production of lipid (e.g., TAG), for example, acetate. In some embodiments, methods and bioreactors are provided for the production of biofuel (e.g. TAG and/or TAG precursors or derivatives, such as fatty acids or biodiesel) from $CO_2$ and $H_2$ or electrons provided by electric current.

In some embodiments, a TAG-producing microorganism capable of converting a carbon substrate, e.g., a carbohydrate feedstock or an organic compound (e.g., acetate), to a TAG that can be used for biodiesel (e.g., fatty acid methyl ester, FAME) production or the production of edible lipids or other TAGs or TAG derivatives as described herein, is employed for TAG production in an aerobic fermentor. In some embodiments, the microorganism is an oleaginous microorganism, for example, an oleaginous yeast. In some embodiments, the oleaginous yeast employed is *Yarrowia lipolytica*. In some embodiments, aerobic TAG fermentation is combined with anaerobic $CO_2$ fixing bacteria operating in a separate anaerobic fermentor. In some embodiments, electrons are provided to the anaerobic fermentor via hydrogen for reducing potential. In some embodiments, electrons are provided to the anaerobic fermentor via current (e.g., via electrodes) for reducing potential. In some embodiments, the product of the anaerobic $CO_2$ fixation is a biofuel, for example, an alcohol, such as ethanol. In some embodiments, the product of the anaerobic $CO_2$ fixation is a carbon substrate, e.g., acetate, that can be used for aerobic fermentation to TAG. In some embodiments, acetate produced by anaerobic $CO_2$ fixation is utilized by the aerobic microorganism for growth and TAG (e.g., oil) production. In some embodiments, the aerobic acetate-to-TAG conversion achieves close-to-theoretical yields.

The economic viability of some of the methods provided herein depends on the rate of $CO_2$ fixation and acetate production. While typical reported volumetric rates are low, specific rates of $CO_2$ fixation by acetogens are reasonable and can be significantly enhanced by applying technologies of metabolic engineering and synthetic biology. Some aspects of this invention provide methods for the engineering and/or isolation of organisms capable of rapid fixation of $CO_2$ and acetate production. In some embodiments, enhanced $CO_2$ fixation is accomplished by engineering the $CO_2$ fixation pathway in a $CO_2$ fixing microorganism, e.g., an acetogenic bacterium, in order to amplify carbon flux. In some embodiments, a natural organism or a mutant derivative of a natural organism that can efficiently accept electrons for $CO_2$ reduction in a reverse microbial fuel cell configuration is isolated and used for $CO_2$ fixation.

Anaerobic $CO_2$ Fixation Using Microbes

In some embodiments, $CO_2$ is converted to a carbon substrate by a microorganism via anaerobic $CO_2$ fixation. In some embodiments, the carbon substrate is a biofuel, for example, an alcohol, such as ethanol. In some embodiments, the carbon substrate is a compound that can be used as a carbon source for aerobic fermentation to a TAG, for example, acetate.

Naturally occurring acetogens (acetogenic bacteria) that can produce acetate by fixing $CO_2$ in the presence of hydrogen or other electron source are well known to those of skill in the art and include, but are not limited to acetogenic *Clostridia*. While the overall rates of acetate production are low, the specific rates are reasonable, such that, if one could achieve a dense culture of approximately OD35-50, while maintaining the same specific rates of $CO_2$ fixation and acetate production, the overall acetate productivity could approach that of ethanol production by yeast. This would make the envisioned process of biodiesel production from $CO_2$ fixation economically feasible at a maximum hydrogen price in the range of $1.50-1.70. In some embodiments, acetogenic microbes are provided that are further enhanced to exhibit increased specific metabolic rates via methods of metabolic engineering and synthetic biology.

Suitable organisms and culture/fermentation conditions for conversion of $CO_2$ to a carbon substrate, for example, acetic acid, butanol, or ethanol are described herein and additional suitable organisms and culture/fermentation conditions are well known to those of skill in the art and include, but are not limited to the organisms and culture or fermentation conditions described in International Patent Application Publication Nos: WO2009/105372; WO2007/117157; WO2008/115080; and WO2009/064200; the entire contents of each of which are incorporated herein by reference. Additional suitable organisms and culture/fermentation conditions include, but are not limited to, those described in Das, A. and L. G. Ljungdahl, Electron Transport System in Acetogens; Drake, H. L. and K. Kusel, *Diverse Physiologic Potential of Acetogens*; Chapters 14 and 13 of Biochemistry and Physiology of Anaerobic Bacteria, L. G. Ljungdahl eds., Springer (2003); U.S. Patent Application Publication No. 2007/0275447 entitled "Indirect Or Direct Fermentation of Biomass to Fuel Alcohol," (e.g., *Clostridium carboxidivorans*); and U.S. Pat. No. 7,704,723 entitled "Isolation and Characterization of Novel Clostridial Species," (e.g., *Clostridium ragsdalei*); the entire contents of each of which are incorporated herein by reference. Additional suitable microorganisms include, but are not limited to, *Butyribac-* terium methylotrophicum (see, e.g., "Evidence for Production of n-Butanol from Carbon Monoxide by Butyribacterium methylotrophicum," Journal of Fermentation and Bioengineering, vol. 72, 1991, p. 58-60; "Production of butanol and ethanol from synthesis gas via fermentation," FUEL, vol. 70, May 1991, p. 615-619); *Clostridium Ljungdahli*, (see, e.g., U.S. Pat. Nos. 6,136,577; 5,173,429, 5,593,886, and 6,368,819; International Patent Application Publication Nos WO 00/68407; WO 98/00558 and WO 02/08438; and European Patent EP 117309); *Clostridium autoethanogenum* (see, e.g., Aribini et al, Archives of Microbiology 161: pp 345-351); *Moorella* sp. (see, e.g., Sakai et al, Biotechnology Letters 29: pp 1607-1612). The entire contents of each of the above listed publications is incorporated herein by reference. In some embodiments, the acetogenic bacterium is a *Clostridium, Moorella, Oxobacter, Peptostreptococcus, Acetobacterium, Eubacterium, Desulfotomaculum, Archaeglobulus* or *Butyribacterium*, for example, *Clostridium carboxidivorans, Butyribacterium methylotrophicum, Clostridium tetanomorphum, Clostridium autoethanogenum, Clostridium ljungdahlii, Clostridium carboxidivorans, Clostridium tetanomorphum, Oxobacter pfennigii, Peptostreptococcus productus, Acetobacterium woodii, Eubacterium limosum, Butyribacterium methylotrophicum, Moorella thermoacetica, Moorella thermoautotrophica, Desulfotomaculum kuznetsovii, Desulfotomaculum thermobenzoicum,* or *Archaeoglobulus fulgidis*. Additional acetogens suitable for use in the methods and anaerobic fermentors disclosed herein will be apparent to those of skill in the art. It will also be appreciated that, while in preferred embodiments a homogeneous culture of acetogens of a single strain is employed, a mixed culture of two or more acetogens may also be used in a $CO_2$ fixation process or fermentor as provided herein.

In some embodiments, the $CO_2$ fixing bacteria (e.g., the acetogen) is cultured in the anaerobic fermentor in a a suitable liquid medium. In some embodiments, the liquid medium comprises vitamins and minerals sufficient to permit growth of the microorganism used. Suitable liquid media for anaerobic microbe culture are known to those of skill in the art and include, but are not limited to, those described in U.S. Pat. Nos. 5,173,429; and 5,593,886; and International Patent Application Publication No WO 02/08438; the entire contents of each of which are incorporated herein by reference.

Acetogenic Bacteria, *Clostridia* and Non-Photosynthetic $CO_2$ Fixation

Many of the non-photosynthetic carbon fixation pathways belong to anaerobic metabolism. These pathways have been hypothesized to be similar to the primordial activity of life billions of years ago, where inorganic compounds were plentiful and organism complexity was very low. Three of them are the (1) Wood-Ljungdahl (W-L) pathway, (2) reductive TCA Cycle, and (3) 3-Hydroxypropionate pathway (12), of which the most prominent is the Wood-Ljungdahl pathway. While other pathways for carbon fixation are cyclic, requiring the recycling of intermediates, the Wood-Ljungdahl pathway is the only linear pathway known to fix carbon. It is further suggested that this pathway may have been the first autotrophic process on Earth (13).

Besides using the Wood-Ljungdahl pathway to grow using $CO_2$ as a sole carbon source, some bacteria (e.g. acetogens) employ this pathway in order to maximize yield when grown with other substrates (e.g., glucose). They do this, for example, by consuming glucose normally by glycolysis, which produces $CO_2$, reducing equivalents (e.g., NADH), and carbon for biomass or product (e.g., pyruvate). In certain circumstances, the cell can recover the $CO_2$ by using those same reducing equivalents to form acetyl-CoA (14). This allows acetogens to exhibit a maximum theoretical yield of 100%. All glucose consumed is metabolized to acetate, rather than the 50-60% as observed in many other organisms (15).

While most organisms employing glycolysis can only produce a net of 2 ATP for every mole of glucose, acetogens are able to produce 4 ATP. However, when using $CO_2$ as the sole carbon source, no net ATP is generated by substrate-level phosphorylation as shown in FIG. 1 and Eq (1). This process produces very little energy, which is captured by ion gradients—probably suggesting these organisms grow rather slowly. Energy stored in ion gradients is converted to ATP by an $F_1F_0$ ATP synthase (16). The overall reaction for the fixation of carbon using this pathway is presented in equation (1). This process is referred to as homo-acetogenesis, or the acetyl-CoA Wood-Ljungdahl pathway.

$$2CO_2 + 4H_2 \rightarrow CH_3COOH + H_2O \qquad (Eq. 1)$$

Each $CO_2$ molecule proceeds down a separate branch of this pathway. One $CO_2$ is activated by an equivalent of ATP, proceeds down the 'methyl (or Eastern) branch', and is reduced to an activated methyl group while the other proceeds down the 'carbonyl (or Western) branch' and is reduced to CO. At this point the two separate branches merge and one molecule of acetyl-CoA is synthesized. This acetyl-COA may then undergo substrate-level phosphorylation, thereby being reduced to acetate and regenerating the ATP used to activate the $CO_2$ molecule that entered the 'methyl branch'.

The 'methyl branch' of the acetyl-CoA Wood-Ljungdahl pathway depends on six different enzymes: formate dehydrogenase, formyl-$H_4F$ synthetase, methenyl-$H_4F$ cyclohydrolase, methylene-$H_4F$ dehydrogenase, methylene-$H_4F$ reductase, and methyltransferase (13). However, the first five of these genes are found in nearly all bacteria and eukaryotes (17). Conversely, the 'carbonyl branch' of the acetyl-CoA Wood-Ljungdahl pathway depends only on the single gene acetyl-CoA synthase (13) and this gene is unique to acetogens, methanogens, and sulfate reducers. Furthermore, the acetyl-CoA synthase enzyme is bifunctional. Not only does it catalyze the reduction to CO, but also the assembly of the carbon from both branches into acetyl-CoA (17). Transformation of this pathway into any model bacteria or yeast, therefore, will only require the heterologous expression of two genes: methyltransferase and acetyl-CoA synthase. In some embodiments, any acetogenic microbe modified to exhibit heterologous expression of methyltransferase and/or acetyl-CoA synthase is suitable for use in the methods and/or fermentors provided herein.

The W-L pathway exists in several organisms, best known among them being the acetogenic *Clostridia*, such as *Clostridium aceticum, Clostridium difficile, Moorella thermoacetica* (formerly *Clostridium*) and, also, *Acetobacterium woodii*. Besides a strong medical interest in these organisms, it is also noted that *Clostridia* have been the organism of choice for the biological production of solvents and butanol (18-19). As a result, there is a large body of research on their growth and physiology, enzymology of many reactions, including those listed above associated with the W-L pathway as well as enzymes catalyzing the Acetone-Butanol-Ethanol (ABE) pathway (20-21). In addition, the genomes of two solventogenic *Clostridia* have been sequenced and numerous studies have examined their transformation with homologous and heterologous genes. Metabolic Engineering of solventogenic *Clostridia* has been advanced in the past 20 years mostly by the work of the Papoutsakis laboratory, which developed vectors, promoters, transformation systems, and numerous strains with varying but well-defined genetic backgrounds in their studies of gene expression, pathway construction and product formation (21-23).

Some aspects of this invention are based on the recognition that deployment of *Clostridia* for $CO_2$ fixation at industrial scale can be achieved by: (a) increasing the capacity of the $CO_2$-fixing pathway by over-expressing properly identified and targeted genes in order to enhance the specific $CO_2$ assimilation rates, and/or, (b) growing $CO_2$-fixing *Clostridia* to high cell densities in order to achieve high volumetric productivities. Some methods and engineered microbes provided herein achieve these goals, either alone or in combination.

Metabolic Engineering of *Clostridia*

In some embodiments, a natural acetogen (preferably *Clostridium aceticum, Clostridium thermoaceticum, Moorella thermoacetica*), is used as the $CO_2$ fixing organism in the anaerobic fermentor. In other embodiments, engineered acetogen strains, for example, of *C. acetobutylicum*, as described elsewhere herein, are employed as the $CO_2$ fixing organism in the anaerobic fermentor.

Some aspects of this invention relate to the improvement of the overall volumetric productivity of acetate production via metabolic engineering of acetogens. Some embodiments provide methods for increasing the acetogen culture density as well as methods for engineering the pathway of acetogenesis to enhance the specific rate of hydrogen adsorption and metabolic processing.

Two seminal advances in the molecular biology of *Clostridia* should be noted. The first is the collective work on engineering the solventogenic pathways that resulted in several very interesting engineered strains. Using a combination of gene (ptb or solR) knockouts with plasmid-borne expression of the aldehyde-alcohol Dehydrogenase (DH) gene aad, generated strains capable of the highest reported solvent (butanol/acetone/ethanol) production in this or any other organism (49-50). More directly related to some aspects of the instant invention, the issue of aerotolerance has been recently attended to (51). It was shown that deletion of a peroxide repressor (PerR)-homologous protein in *C. acetobutylicum* resulted in prolonged aerotolerance, limited growth under aerobic conditions, higher resistance to $H_2O_2$, and rapid consumption of oxygen. This has practical implications in allowing the cells to carry out partial aerobic metabolism for increasing cell densities and resolving electron flow bottlenecks.

Another major advance in the field of clostridial biotechnology is the abolition of sporulation while maintaining solvent formation. This was accomplished by disrupting the genes coding for two major sporulation-specific sigma factors (SigE and SigG) (52). In a different approach, asporogenous, non-solventogenic strains (such as strains M5 and DG1 of *C. acetobutylicum*, which have lost the pSOL1 megaplasmid (53)) were used as a starting point and the desirable solvent formation genes were re-introduced or overexpressed. This resulted in high yielding strains whose product distribution could be additionally controlled (22).

In some embodiments, an acetogenic strain of *clostridia* is employed for anaerobic CO2 fixation that exhibits one or more modifications as described herein, for example, a peroxide repressor deletion, which allows growth at increased densities.

Metabolic Engineering for Enhancing Acetate Formation in *C. acetobutylicum*

In some embodiments, a metabolically engineered *C. acetobutylicum* is provided that directly utilizes $CO_2$ and $H_2$ for the production of acetate and biomass. In some embodiments, genes from the Wood-Ljungdahl pathway are isolated from other mesophilic or thermophilic clostridia and cloned into *C. acetobutylicum*. *C. acetobutylicum* does not have a complete, native Wood-Ljungdahl pathway but does have a number of homologs to components of the W-L pathway (Table 1).

TABLE 1

Homologs of the W-L pathway in *Moorella thermoacetica, C. difficile* and *C. acetobutylicum*.

| | Genes of Woods-Ljungdahl pathway in: | | | Protein identity between: | | |
|---|---|---|---|---|---|---|
| | *M. thermoacetica* (MTA) | *C. acetobutylicum* (CAC) | *C. difficile* (CDF) | MTA/CAC | MTA/CDF | CDF/CAC |
| Eastern | Moth_2312 | — | CD3317 | — | 32.7% | — |
| | Moth_2314 | CAC0764 | CD1537 | 21.5% | 26.6% | 37.1% |
| | Moth_0109 | CAC3201 | CD0718 | 64.8% | 66.2% | 62.1% |
| | Moth_1516 | CAC2083 | CD0720 | 44.1% | 42.1% | 37.1% |
| | Moth_1191 | CAC0291 | CD0722 | 12.5% | 38.6% | 13.1% |
| Western | Moth_1197 | CAC0578 | CD0727 | 6.3% | 37.6% | 6.8% |
| | Moth_1201 | — | CD0726 | — | 37.8% | — |
| | Moth_1198 | — | CD0725 | — | 38.0% | — |
| | Moth_1203 | CAC2498/0116 | CD0716 | 29.8%/27.5% | 38.5% | 30.2%/29.8% |
| | Moth_1202 | — | CD0728 | — | 46.1% | — |

The first homolog is the β-subunit of the formate dehydrogenase, which reduces $CO_2$ to formate and is the first reaction in the "Eastern" branch of the pathway. In *M. thermoacetica*, this enzyme is made up of α and β subunits, Moth_2312 and Moth_2314, respectively. However a potential homolog was only found for the β-subunit and it is not known why *C. acetobutylicum* would have a functional β-subunit without an α-subunit. Interestingly, the β-subunit homolog in *C. difficile* is not located near the α-subunit, as would be expected. It is possible *C. difficile* only needs the one enzyme CD3317 to reduce $CO_2$ to formate. For the remaining enzymes in the Eastern branch, good homologs were found except for one. CAC0291 has poor homology but is a bifunctional enzyme in *C. acetobutylicum*, which codes for both the needed methylenetetrahydrofolate reductase and a homocysteine S-methyltransferase.

Unlike the Eastern branch, *C. acetobutylicum* is missing most of the enzymes from the Western branch. The only good homologs which were found in *C. acetobutylicum* are two carbon monoxide dehydrogenases. A second potential homolog is a methyltetrahydrofolate methyltransferase, CAC0578, which has very poor protein identity with the corresponding enzyme in both *M. thermoacetica* and *C. difficile*. However, CAC0578 is annotated as being able to catalyze the reaction from methyl-H$_4$folate to H$_4$folate, the reaction that the *M. thermoacetica* and *C. difficile* enzymes carry out. The remaining components of the Wood-Ljungdahl pathway, the corrinoid iron-sulfate protein (CFeSP) and the acetyl-CoA synthase, have no homologs in *C. acetobutylicum*. It is significant to note that all these homologs identified in *C. acetobutylicum* (and all genes belonging in the same operon with those) are highly expressed throughout the course of the culture of *C. acetobutylicum*. These data were obtained from a very detailed global gene expression study of *C. acetobutylicum* (54). Thus, we anticipate that expression of these genes will not be limiting the ability to institute the W-L pathway in *C. acetobutylicum*.

In some embodiments, at least four genes will be cloned into *C. acetobutylicum* to generate a complete Wood-Ljungdahl pathway (Table 1): a formate dehydrogenase (e.g., CD3317, 2.1 kb), the CFeSP α-subunit (e.g., CD0726, 1.4 kb), the CFeSP β-subunit (e.g., CD0725, 0.9 kb), and an acetyl-CoA synthase (e.g., CD0728, 2.1 kb). In addition, a methyltetrahydrofolate methyltransferase (e.g., CD0727, 0.8 kb) and the (3-subunit of the formate dehydrogenase (e.g., CD1537, 1.4 kb) may also be introduced. In some embodiments, these genes are *C. difficile* genes, since *C. difficile* has a complete W-L pathway and is a closer relative to *C. acetobutylicum* than *M. thermoacetica*. In some embodiments, because of the number and size of the genes, at least two plasmids are used to express the genes in *C. acetobutylicum*. In some such embodiments, in order to facilitate a plurality of plasmids to exist together in *C. acetobutylicum*, the different plasmids comprise different origins of replication. For example, in some embodiments, one of the expression vectors uses the origin of replication from the *B. subtilis* plasmid pIM13, obtained from the *C. acetobutylicum* plasmid pIMP1 (55), and the second origin is derived from the C. butyricum plasmid pCBU2, obtained from the *C. acetobutylicum* plasmid pSYL2 (56). In some embodiments, the gene needed to complete the Eastern branch, CD3317, is placed on one plasmid under the control of the thiolase (thl) promoter, a strong clostridial promoter (57-58), while the three genes needed to complete the Western branch, CD0725, CD0726, and CD0728, are placed on the second plasmid as an operon under control of the phosphate butyryltransferase (ptb) promoter, another strong clostridial promoter(23, 57).

In some embodiments, engineered strains are grown in serum bottles using a modified Hungate technique (59) in defined media (60) under CO$_2$/H$_2$. Briefly, small test tubes are filled with nonsterile, defined media, and gassed using CO$_2$. After gassing, a butyl rubber stopper is used to seal the tube and a crimped metal seal is added. The tube and media are then autoclaved. Before inoculation, the tubes are filled with H$_2$ and CO$_2$ (80:20, v/v) to a final pressure of 0.2 MPa. These conditions were successfully used for *Moorella* sp. HUC22-1 (61-62). Other conditions will be apparent to those of skill in the art and the invention is not limited in this respect. In some embodiments, a defined clostridial medium (60) is used with minimal glucose (1 to 80 g/L can be used).

In some embodiments, CO$_2$ uptake and utilization in *C. acetobutylicum* is monitored during bioproces sing. In some embodiments, the concentration of CO$_2$ and H$_2$ is measured in the headspace of the anaerobic fermentor throughout the fermentation via gas chromatography (62), and similar to previously described methods (63). In some embodiments, the recombinant strains are able to consume the CO$_2$ and H$_2$ while the wild-type control show minimal to no consumption. A second assay uses C$^{13}$ labeled carbon dioxide, similar to the original Wood paper investigating the pathway (64). In some embodiments, *C. acetobutylicum* is grown on defined media with minimal glucose and C$^{13}$O$_2$/H$_2$ pumped into the head space. After the fermentation, acetate is isolated and run through a mass spectrometer to determine the relative amount of heavy acetate with C$^{13}$ to non-heavy acetate. In some embodiments, the recombinant *C. acetobutylicum* with the W-L pathway is able to produce heavy acetate, while the control wild-type is not able to produce heavy acetate.

In some embodiments, the gene from *C. difficile*, CD0727, is added to the Western operon on one of the expression plasmids, to make an operon of CD0725-CD0726-CD0727-CD0728. In some embodiments, this expression plasmid is transformed into a *C. acetobutylicum* strain harboring only the Eastern expression plasmid to obtain a strain capable of high rates of CO$_2$/H$_2$ consumption. In some embodiments, the β-subunit of the formate dehydrogenase from *C. difficile* will be added to the Eastern expression plasmid and transformed into a *C. acetobutylicum* strain harboring the larger Western expression plasmid. In some embodiments, the genes related to the Wood-Ljungdahl pathway are cloned from *M. thermoacetica* (instead of from *C. difficile*) and overexpressed in *C. acetobutylicum*.

In some embodiments, to further enhance CO$_2$ and H$_2$ utilization by the acetogen, the native CAC genes are overexpressed in the acetogen (Table 1). In some embodiments, the native hydrogen-uptake genes (namely: CAC0028-hydA, CAC0808-0811-hybG-hypE-hypF-hypD, CAC3230-ferredoxin, CAP0141-0143-mbhS-mbhL-hyaD) are overexpressed in the acetogen using strong promoters, like the ptb, thl, and the pta (phosphotransacetylase) promoters.

In some embodiments, random chemical mutagenesis (65) or transposon mutagenesis (66-68) is employed to screen for an acetogenic strain that uses CO$_2$ and H$_2$ at high rates. In some embodiments, the genes that are introduced into the microbe to generate the Wood-Ljungdahl pathway are integrated into the microbial chromosome using a markerless technology (69).

Aerobic TAG Production Using Oleaginous Microbes

Figure 3A:
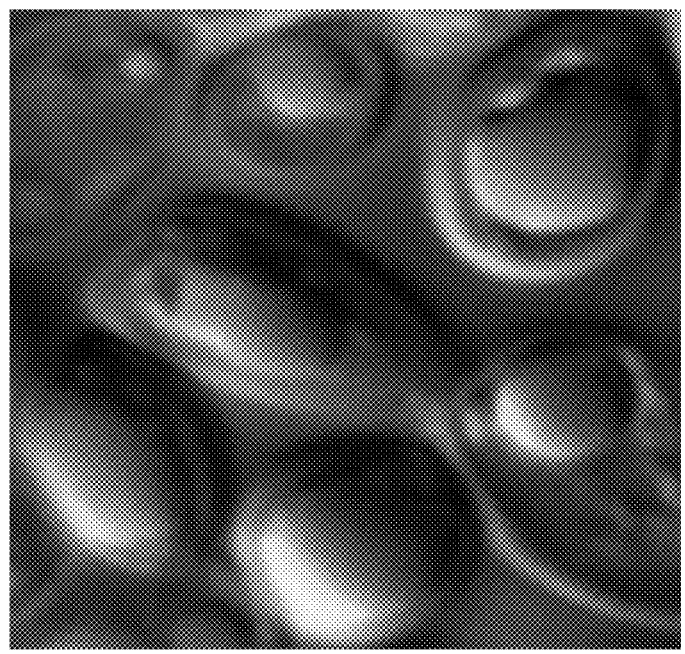
FIG. 3A. Oleaginous microbe.
Figure 3B:
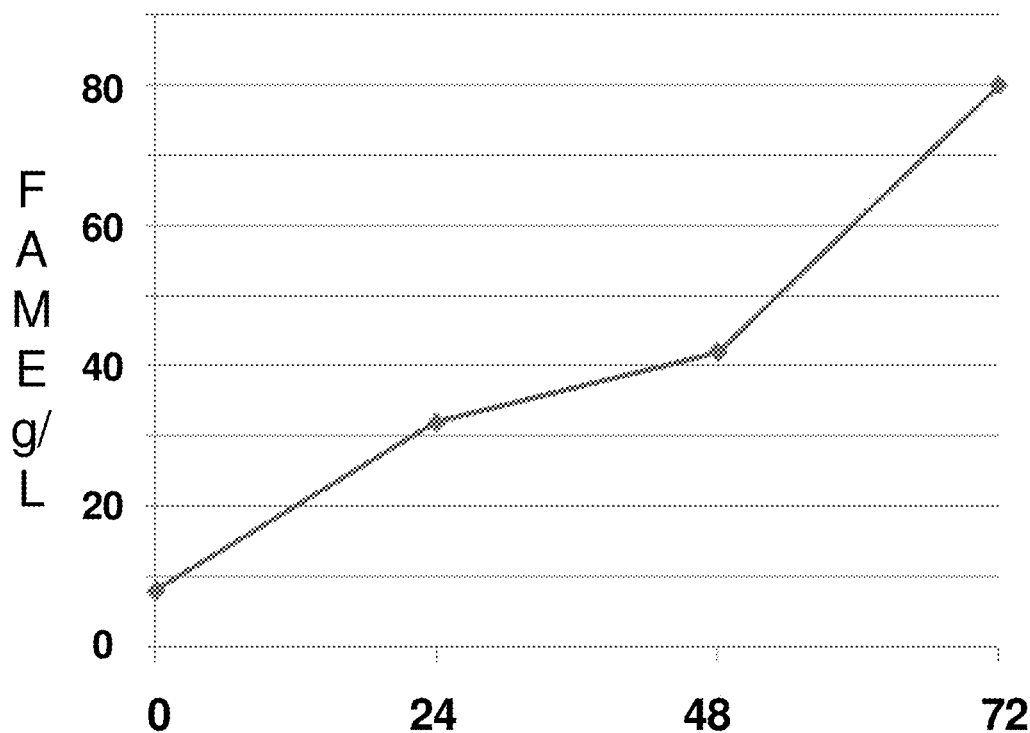
FIG. 3B. time course (hrs) of oil accumulation in fermentor.
Figure 4:
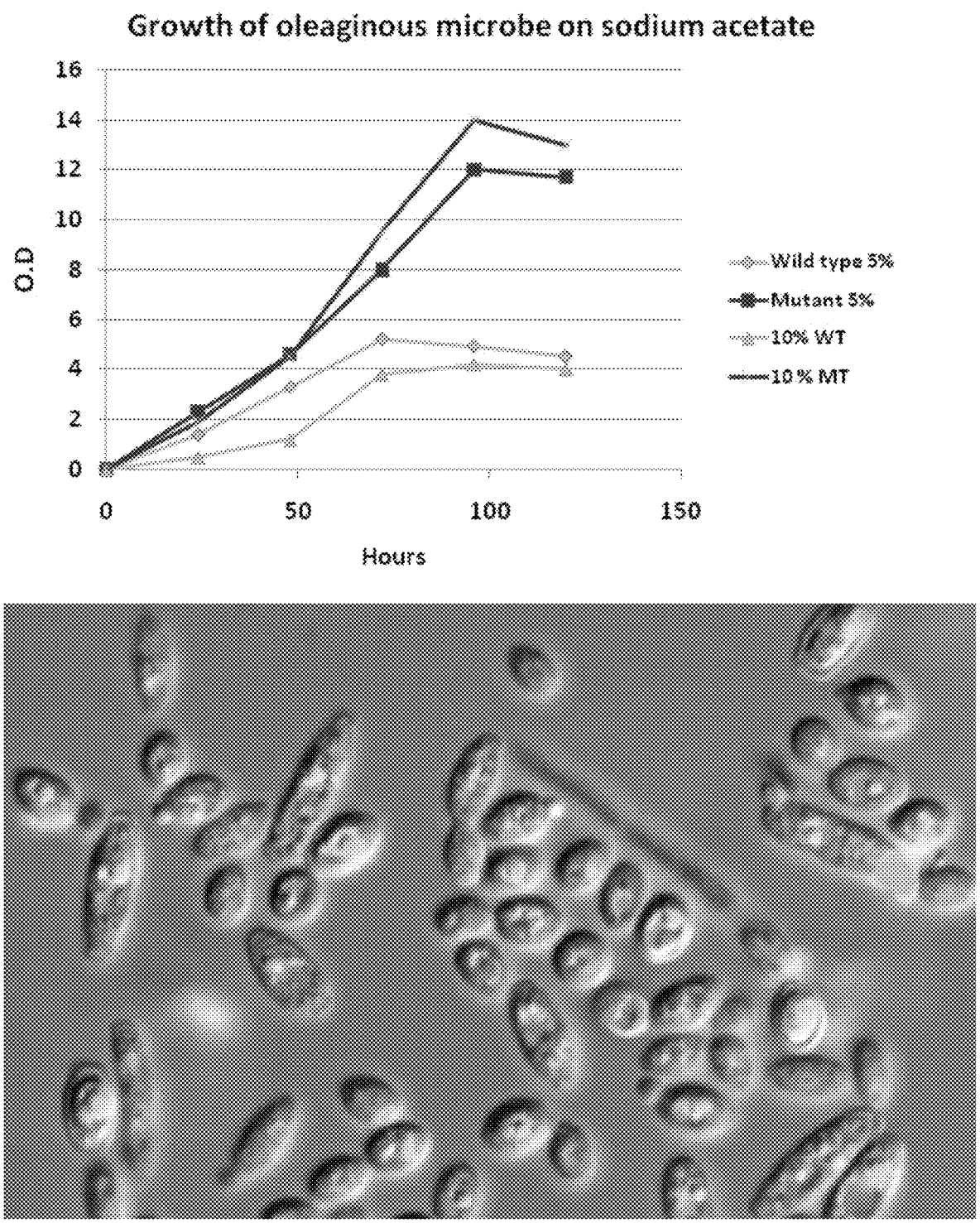
FIG. 4. Growth and oil production of oleaginous microbe on acetate.

In some embodiments, a carbon source, for example, a carbohydrate source, is converted in an aerobic fermentation process to a lipid or oil, for example, to a TAG. In some embodiments, the aerobic fermentation process is carried out by a microorganism or microbe. In some embodiments, the microorganism is an oleaginous microorganism, for example, an oleaginous yeast. In some embodiments, the microorganism is a microorganism described in U.S. provisional application U.S. Ser. No. 61/309,782, filed Mar. 2, 2010, the entire contents of which are incorporated herein by reference. In some embodiments, the microorganism is *Yarrowia lipolytica*. In some embodiments, the microorganism is a genetically engineered oleaginous microorganism, for example, a *Y. lipolytica* that overexpresses a stearoyl-CoA Desaturase (SCD) gene. In *S. cerevisiae*, a stearoyl-CoA desaturase gene was identified as Ole1 in 1990 (Stukey J E, et al., J Biol Chem., 1990, 265(33):20144-9). The human stearoyl-CoA desaturase gene was partially characterized in 1994 via isolation of a 0.76 kb partial cDNA from human adipose tissue (Li et al., Int. J. Cancer, 1994, 57, 50 348-352). The gene was fully characterized in 1999 and it was found that alternative usage of polyadenylation sites generates two transcripts of 3.9 and 5.2 kb (Zhang et al., Biochem. J., 1999, 340, 255-264). In *S. cerevisiae*, fatty acid monodesaturation is catalyzed by the endoplasmic reticulum (ER)-resident and essential Δ9-desaturase, Ole1 (Martin C E, Oh C S, Jiang Y, *Regulation of long chain unsaturated fatty acid synthesis in yeast*. Biochim Biophys Acta. 2007 March; 1771(3):271-85. Epub 2006 Jul. 13. An exemplary oleaginous yeast overexpressing an SCD gene is depicted in FIG. 3. Such microbes can utilize various carbon sources for growth and TAG production, including acetate. FIG. 4 shows that an exemplary *Y. lipolytica* overexpressing an SCD gene is able to thrive at acetate concentrations of 10%, making it an ideal candidate for the TAG production methods and bioreactors described herein.

*Y. lipolytica* is a non-pathogenic oleaginous yeast that can use a variety of carbon sources, including organic acids, hydrocarbons and various fats and oils. The term "oleaginous" refers to a microbe that can accumulate more than 20% of its dry cell weight as lipid (see C. Ratledge et al., *Microbial routes to lipids*. Biochem Soc Trans. 1989 December; 17(6):1139-41). According to some aspects of this invention, *Y. lipolytica* represents a microbe for biofuel or biofuel precursor production, because *Y. lipolytica* is an obligate aerobe with the ability to assimilate carbohydrates, for example, glucose, or glycerol as a sole carbon source, and, compared to other yeast strains, *Y. lipolytica* has a higher glucose to fatty acid and triacylglycerol (TAG) flux and higher lipid storage capacity. See, e.g., Beopoulos A, Cescut J, Haddouche R, Uribelarrea J L, Molina-Jouve C, Nicaud J M, *Yarrowia lipolytica* as a model for bio-oil production. Prog Lipid Res. 2009 November; 48(6):375-87. Further, *Y. lipolytica* is one of the more intensively studied 'non-conventional' yeast species and genome sequencing, including mitochondrial DNA, of *Y. lipolytica* was completed recently. Kerscher S, Durstewitz G, Casaregola S, Gaillardin C, Brandt U., The complete mitochondrial genome of *Yarrowia lipolytica*. Comp Funct Genomics. 2001; 2(2):80-90. The availability of genomic sequence data makes genetic manipulation more accessible, even though functional annotation of genomic sequences is not complete. See, e.g., Sokolova L, Wittig I, Barth H D, Schagger H, Brutschy B, Brandt U., LILBID-mass spectrometry of protein complexes from blue-native gels, a sensitive top-down proteomic approach. Proteomics. Published online 2010 Feb. 1, PMID: 20127694.

Some aspects of this invention relate to an aerobic microbe engineered and/or optimized for large-scale TAG or TAG precursor production. In some embodiments, the engineered aerobic microbe comprises an increased SCD gene product activity. In some embodiments, the microbe exhibits an increased fatty acid synthesis rate, an increased TAG storage, and/or an additional required or desirable trait.

In some embodiments, the engineered aerobic microbe is an oleaginous yeast, for example, *Y. lipolytica* overexpressing an SCD gene. In some embodiments, the engineered yeast exhibits highly desirable and unexpected phenotypic characteristics, for example: increased carbon to oil conversion approaching theoretical values, robust growth, continuous oil production, remarkable biomass production, and increased tolerance of the carbon source and associated substances. In some embodiments, the engineered yeast provided by aspects of this invention exhibits a carbon to oil conversion of about 0.025 g/g (g TAG produced/g Glucose consumed), about 0.5 g/g, about 0.75 g/g, about 0.1 g/g, about 0.15 g/g, about 0.2 g/g, about 0.25 g/g, about 0.29 g/g, or about 0.3 g/g, approaching theoretical values, continuous oil production. In some embodiments, the engineered yeast provided by aspects of this invention exhibits a biomass production that is increased about 2-fold, about 2.5-fold, about 5-fold, about 7.5-fold, about 10-fold, about 15-fold, about 20-fold, about 25-fold, about 30-fold, about 32-fold, about 35-fold, or about 40-fold as compared to wild type yeast. In some embodiments, the engineered yeast provided by aspects of this invention exhibits tolerance to the carbon source and associated substances at concentrations of up to about 150%, up to about 175%, up to about 200%, up to about 225%, up to about 250%, up to about 275%, up to about 300%, up to about 325%, up to about 350%, up to about 375%, up to about 400%, or up to about 500% of that of the highest concentrations tolerated by wild type yeast.

Bioreactors for TAG Production

Some embodiments of this invention provide bioreactors for the production of TAG by biological fermentation. FIGS. 2*a* and 2*b* depict two exemplary bioreactors that include separate aerobic and anaerobic fermentors for the aerobic conversion of a carbon substrate to a TAG and the anaerobic fixation of $CO_2$, respectively. In some embodiments, an integrated bioreactor system is provided that comprises an aerobic fermentor for the growth of an oleaginous microbe and/or TAG production, and an anaerobic fermentor where fixation of $CO_2$ and production of a carbon substrate (e.g., acetate) take place, wherein the $CO_2$ produced during growth/TAG production is used for the anaerobic production of the carbon substrate and/or wherein the carbon substrate (e.g., acetate) is used as the carbon source for the aerobic growth/TAG production (FIG. 2*b*). In some embodiments, the aerobic fermentation process uses a carbohydrate feedstock as a carbon source. In other embodiments, however, no carbohydrate feedstock is used but the entire bioprocessing is run on $CO_2$ as the sole carbon source. In some embodiments, $CO_2$ is assimilated along with hydrogen or electrons via a biocathode from an external electric current and reduced to a reduced carbon substrate by a $CO_2$ fixing bacterium, for example, an acetogenic bacterium, that is either engineered or is natively capable of producing reduced carbon substrates, e.g. ethanol, acetate or butyrate. In some embodiments, the carbon substrate is used as a carbon source in the aerobic fermentor for oil production by an oleaginous microbe. In some embodiments, the net input is $CO_2$ and $H_2$ or electricity, and the net output is TAG, e.g., oil for biodiesel production. In some embodiments, part of the $CO_2$ introduced into the anaerobic fermentor is recycled from the aerobic TAG-producing fermentor.

In some embodiments, the anaerobic fermentor is used to capture $CO_2$ produced in an aerobic fermentation process, for example, in the production of TAG by an oleaginous microbe, and the captured $CO_2$ is converted into a biofuel (e.g., ethanol) by culturing an appropriate *Clostridium* strain in the presence of the $CO_2$ and hydrogen under anaerobic conditions. In some embodiments, this "$CO_2$ recycling" yields almost double the amount of biofuel produced from a certain amount of carbohydrate feedstock. An exemplary bioreactor according to this concept is depicted in FIG. 2*a*.

The anaerobic fermentors described herein provide anaerobic conditions, which refers to conditions that are substantially devoid of oxygen. The aerobic fermentors described herein provide aerobic conditions, which refers to conditions in which oxygen is present, abundant, or overabundant. In some embodiments, the conditions within the fermentors are monitored prior to and/or during the bioprocessing carried out to generate TAG as described herein. For example, in some embodiments, the anaerobic fermentor comprises a turbidometer to assess the cell density of anaerobic acetogens; a gas chromatography apparatus to assess $CO_2$ and $H_2$ partial pressures at the input and output of the fermentor; a mass flow meter to assess the gas flow rate; a pH meter to assess the acidity of the media; a thermometer to assess the temperature, and/or an HPLC apparatus to assess the acetate concentration and/or the concentration of other carbon substrates produced, for example, of ethanol, butyrate, or organic acids. Similarly, in some embodiments, the aerobic fermentor comprises a turbidometer to assess the cell density of the oleaginous microbe, an HPLC apparatus to assess the concentration of the carbon source (e.g., acetate) in medium, or the concentration of other organic compounds serving as the carbon source, (e.g., citrate, organic acids), a gas chromatography apparatus to measure oxygen and carbon dioxide partial pressures at inflow and/or outflow; a mass flow meter to measure the gas flow rate; a pH meter to measure the acidity of the media, and/or a thermometer to measure the temperature of the media. In some embodiments, the fermentors further comprise one or more controllers that receive input from any combination of the above listed measuring devices and adjust the respective parameter to fall within a desired range or to approximate a desired value. Methods and devices to adjust the parameters indicated above, for example, heaters and coolers for the regulation of temperature, gas inflow and outflow valves, etc., are well known to those of skill in the art, and the invention is not limited in this respect.

In some embodiments, the bioreactor further comprises a carbon substrate (e.g., acetate, butyrate, etc.) concentration device comprising two dialysis units, the first for the extraction of the carbon substrate from the fermentation medium of the anaerobic fermentor using an amine such as ALAMINE® 336 and the second, containing a caustic solution, for the extraction of the carbon substrate from the ALAMINE® 336 solution. This method can, for example, be used for the concentration of butyrate from fermentation broths achieving concentrations of butyrate of approximately 300 g/L.

In some embodiments, the free cell anaerobic fermentor is replaced by a packed bed that employs fibers as immobilization support for the anaerobic acetogens. The purpose of the introduction of a fiber bed immobilized cell reactor is to increase the volumetric productivity of acetate production through a continuous operation without washing out the anaerobic acetogens. In some embodiments, this approach yields a ten-fold increase in the volumetric productivity of the acetogen. In some embodiments, the packed bed fermentor is continuously or semi-continuously seeded with acetogens from a free-cell culture vessel.

In some embodiments, the aerobic fermentor of the bioreactor comprises a microorganism described in U.S. provisional application U.S. Ser. No. 61/309,782, filed Mar. 2, 2010, the entire contents of which are incorporated herein by reference. For example, in some embodiments, the aerobic fermentor comprises a *Y. lipolytica* that overexpresses an SCD gene product. In some embodiments, the anaerobic fermentor of the bioreactor comprises an engineered $CO_2$ fixing bacterium, for example, an engineered acetogen, such as an engineered strain of *C. acetobutylicum* provided herein.

In some embodiments, the aerobic fermentor comprises an rMFC as described in more detail elsewhere herein to achieve $CO_2$ fixation using electrons instead of hydrogen.

Figure 2:
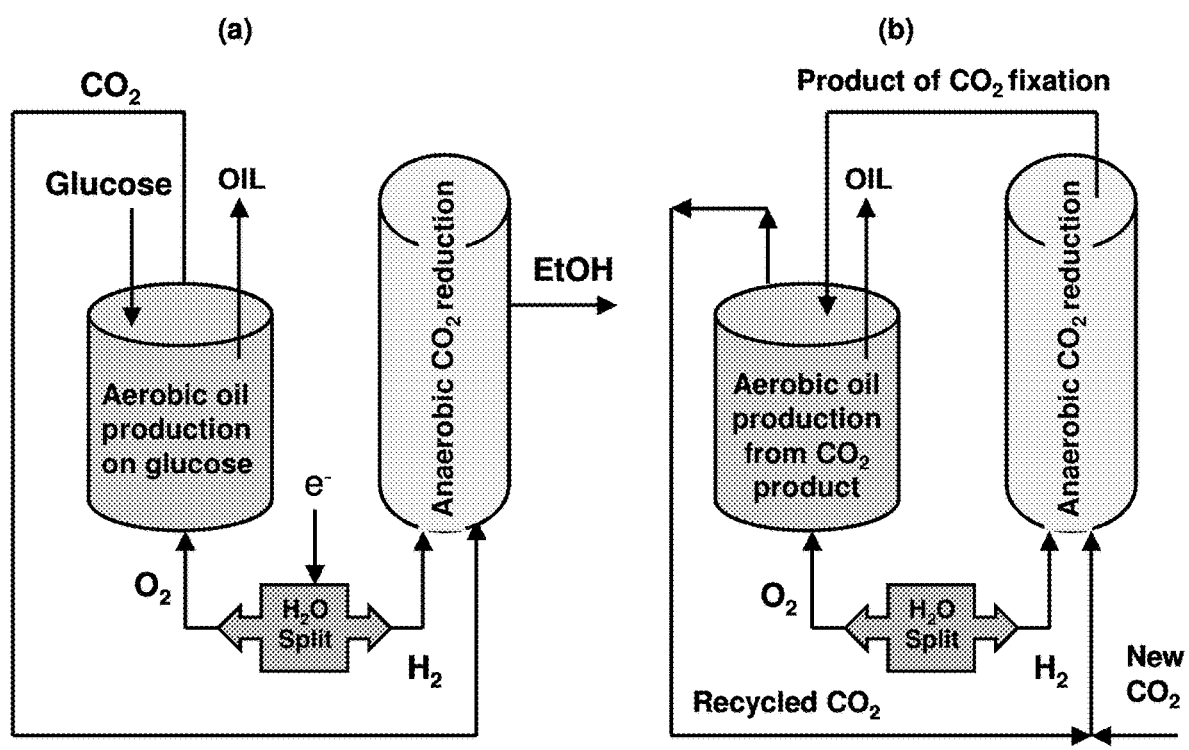
FIG. 2. Schemes of combining an aerobic oil producing fermentation with an anaerobic $CO_2$ fixing process.

In some embodiments, the bioreactor further comprises an electrolytic cell for electrolytic water splitting for the production of oxygen and hydrogen as depicted in FIG. 2. In some embodiments, an electrolytic water-splitting device is used for the generation of the hydrogen stream of the anaerobic fermentor and the oxygen super-saturated (e.g., via microbubble formation) stream of the aerobic fermentor. In some embodiments, the generated $O_2$ is directed to the aerobic fermentor and/or the generated $H_2$ is directed to the anaerobic fermentor. In some embodiments, the aerobic fermentation process is carried out in a liquid in the aerobic fermentor and the $O_2$ produced by electrolysis of $H_2O$ is dispersed in micro-bubbles with increased surface area within the liquid and, hence, much higher volumetric mass transfer coefficient for oxygen in the aerobic fermentor than typical spargers can produce. In some embodiments, this advance contributes to achieving high cell densities (OD 350), for example, the cell densities that yielded the high oil concentrations shown in FIG. 3.

In some embodiments, anaerobic conditions are maintained in the anaerobic fermentor through purging of oxygen traces using initially a $CO_2$ stream and, during operation, a mixture of $CO_2$ and hydrogen. In some embodiments, *C. acetobutylicum* engineered to exhibit the aerotolerance phenotype by deleting the peroxide repressor (PerR)-homologous protein are employed as the $CO_2$ fixing microbes of the anaerobic fermentor.

Biocathodes and Reverse Microbial Fuel Cells (rMFC)

Some aspects of this invention are based on the recognition that recent developments in Microbial Fuel Cells suggest that extracellular electron transfer (EET) can occur from a biocathode to a microbial culture and provide the reducing equivalents needed for $CO_2$ reduction in a reverse MFC configuration. Various strains of *Clostridia* have been found capable of catalyzing the oxidation of reduced organic compounds with the concomitant generation of electrons, transferred via an anode to an external circuit of a traditional microbial fuel cell (MFC). Most MFC research has focused on microbes capable of donating electrons to the anode from degradation of organic matter. Some embodiments of this invention provide a reverse operation at the anode, where electrons from an external source (e.g. a battery) act as reducing agents of an oxidized compound, such as $CO_2$, through the action of microorganisms harboring the relevant (W-L) pathway, and thus capable of carrying out the reduction reactions. Such embodiments are supported by recent studies where abiotic cathodes were replaced with biocathodes, in which enzymes enhance reduction catalysis (24).

The efficacy of a biocathode in any bioelectrochemical system (BES) is typically directly related to the current density (amps per unit area) and coulombic efficiency (% of electrons recovered by the target product). Notably, as microorganisms in a biocathode evolve strategies that lower the cathode overpotentials, higher current densities can be obtained. Typically, autotrophic microorganisms are believed to be the key players on biocathodes since the cathode acts as the electron donor for metabolism. As a consequence, $CO_2$ (or bicarbonate) can be reduced (or fixed), though to date there are few studies that directly examine biocathode carbon reduction as described elsewhere herein.

Several studies have examined microbial diversity on MFC cathodes. In one study (25) it was observed that *Pseudomonas flourescens* constituted nearly 50% of the microbial load on a microbial fuel cell deployed in the ocean. In another study, α- and γ-Proteobacteria were identified as the dominant "phylotypes" enriched on the biocathodes under nitrogen limited conditions (26). Rabaey and co-workers also found enrichment of Bacteroidetes, β- and γ-Proteobacteria from mixed sediment-sludge inoculums (27).

Few studies to date have directly examined the linkage between cathode electron donation and microbial metabolic processes. Electron donation from electrodes has been shown to support and stimulate denitrification, methanogenesis, perchlorate reduction, and other reductive processes. Denitrification is a microbially mediated process in which microorganisms respire an inorganic electron donor while using nitrate, nitrite, nitric oxide or nitrous oxide as electron acceptor (28). In 1966, the use of a nitrate reducing biocathode was proposed (29). However, it was not until 2004 that Gregory and co-workers demonstrated for the first time the ability of microbial isolates, enriched from a sediment, to retrieve electrons directly from a cathode (poised at approximately −0.300 V vs. a standard hydrogen electrode) for nitrate to nitrite reduction (30). This was an enrichment of γ-proteobacteria, Gram-positive bacteria and Geobacter-like phylotypes (δ-proteobacteria). Indeed, a pure culture of Geobacter metallireducens was shown to reduce nitrate to nitrite by a cathode poised at −0.300 V vs. SHE. When different sludge and sediment mixtures were used as inocula for a denitrifying biocathode, the complete denitrification from nitrate to $N_2$ was observed (31). Notably, for denitrifying biocathodes, the equilibrium cathode potential is typically around 0V vs. SHE.

Perchlorate reduction with the help of an anoxic biocathode was first demonstrated in the presence of 2,6-anthraquinone disulfonate (AQDS), an extra cellular electron mediator (32). Perchlorate is widely used as a propellant in the aerospace and defense industries, and is of environmental concern due to its high mobility and inhibiting effect on thyroid function (33). Recently, a novel strain was isolated with the ability to reduce perchlorate at −0.300 V vs. SHE in the absence of AQDS (33). Moreover, Rozendal and co-workers suggested the possibility of methanogenesis by methanogens in a biocathode as well as hydrogen production (34). Recently, a biocathode biofilm dominated by *Methanobacterium palustre* was shown to produce methane in a direct way without hydrogen as an intermediate (35). Since biocathodes appear to be able to produce hydrogen and methane in a direct way, biocathodical acetogenesis is also very likely (36). The reduction of fumarate to succinate has also been observed by *Geobacter sulfurreducens* (30) and *Geobacter lovleyi* (37) on graphite cathodes, in the absence of hydrogen or externally added electron mediators. Finally, *Geobacter sulfurreducens* was also shown to reduce uranium (VI) to relatively insoluble uranium (IV) in an anaerobic biocathode poised at approximately −0.300 V vs. SHE (38). In all cases the means by which these microbes harvest electrons from the cathodes remains unknown.

In some embodiments of this invention, metabolic reduction of $CO_2$ is achieved on a biocathode of a reverse microbial fuel cell (rMFC). In some embodiments, the rMFC provides electrons to a $CO_2$ fixing bacterium, e.g., an acetogen, for the reduction of $CO_2$ to a carbon substrate. In some embodiments, the rMFC comprises an amperemeter to measure the current supplied, a turbidometer to measure the density of the cells in the rMFC, and/or a gas chromatography apparatus to measure the partial pressure of $CO_2$ at the inflow and/or the outflow.

Bioelectrochemical System Architecture

MFCs are a type of bio-electrochemical reactors that allow one to harness energy (as electrical current) from microbial metabolism. MFCs typically consist of an anaerobic chamber that houses the anode, a fuel (e.g. compost or wastewater) and associated microbes. The MFC's aerobic chamber houses the cathode and, in some cases, associated microbes. At the anode, microbes oxidize organic matter using the electrode as the oxidant, and hence transfer electrons to the anode. At the cathode, reactions such as the formation of water from protons and oxygen balance the oxidation reactions at the anode. Most studies to date have focused on harnessing electricity from microbial degradation of organic matter in the anode chamber, with the intention of using MFCs for alternative energy generation. However, many studies have shown that the coulombic efficiency (the percentage of electrons available in the fuel that are captured by the anode) of anodic power generation is low when complex fuels are used. Given the limitations of MFC power production, a number of researchers believe that the greatest potential of such bioelectrochemical systems (or BESs) is for the generation of fuels and other commodities (39). For example, investigators have recently developed a BES that generates hydrogen gas at the cathode (40-41). In this reactor, bacteria at the anode oxidize carbon substrates, generating protons and electrons as in a MFC. However, in lieu of providing oxygen to the cathode, current is supplied from an external power source, stimulating the production of hydrogen. Since the protons and electrons are being derived from organic matter through biocatalysis, the voltage needed to generate $H_2$ is an order of magnitude lower than that needed for electrolysis of water. For example, this system uses the equivalent of 0.2 mol hydrogen energy per mole of hydrogen produced, compared to the 1.7 mol loss typical of electrolysis (41). A variety of other products have already been generated using BESs including glutamic acid (42), propionic acid (43), succinate (44), sulfur (45), methane (46), formate (47), and ethanol (48).

Electricity for embodiments using a biocathode or rMFC can be supplied by various means, including combustion of biomass or municipal waste that can also generate the $CO_2$ used in the process.

The functions and advantages of these and other embodiments of the present invention will be more fully understood from the example section below. The following examples section is intended to illustrate the benefits of the present invention and to describe particular embodiments, but does not exemplify the full scope of the invention. Accordingly, it will be understood that the examples section is not meant to limit the scope of the invention.

EXAMPLES

Example 1: Aerobic TAG Production Using Engineered Microbes

In some embodiments, the engineered microbe used for aerobic carbon source to TAG fermentation is capable of converting, at almost maximum theoretical yields, carbohydrates to oils and fats for biodiesel production (see FIG. 3). In some embodiments, the oleaginous microbe is a *Y. lipolytica* overexpressing a stearoyl-CoA desaturase (SCD) gene, which has been identified as a key regulator of carbohydrate to lipid conversion. In some embodiments, the oleaginous microbe comprises an increased activity of an SCD gene product. In some embodiments, the oleaginous microbe further comprises a genetic modification that increases expression of one or more genes chosen from the group of Hemoglobin, Cytochrome, GLUT, Malic Enzyme, ACC, SCD, FAA1, ACS, ACS2, FAT1, FAT2, PCS60, ACLY, FAS, Acyl-CoA synthetase, Pyruvate carboxylase, and AMPK genes, and/or a genetic modification that reduces expression of a JNK2 gene. In some embodiments, the oleaginous microbe is engineered to expresses a native gene as described above under the control of a strong, heterologous promoter. In some embodiments, the oleaginous microbe expresses a heterologous gene as described above, for example, a mammlian (e.g., a murine or human) SCD, hemoglobin, cytochrome, GLUT, ME, etc., gene under the control of a constitutive promoter. For example, in some embodiments, a *Y. lipolytica* expressing a murine or human SCD gene under the control of a constitutive promoter is employed.

In some embodiments, concentrations between 80-100 g/L of biodiesel are achieved within 3 days in aerobic fermentors at conversion yields of ~0.26-0.29 grams of biodiesel per gram of glucose consumed. The stoichiometry of the oil synthesis pathway of the aerobic fermentor (assuming tripalmitin to be representative of the oil composition) is:

$$14C_6H_{12}O_6 + 11.5O_2 \rightarrow 1C_{51}H_{98}O_6 + 33CO_2 + 15.5ATP \qquad (Eq.\ 2)$$

If the ATP produced in the above overall reaction were to be used for the fixation of $CO_2$ this would reduce the glucose requirement by only 0.25 moles, indicating that oil (tripalmitin) synthesis is already energetically optimized. This performance suggests that biodiesel can be produced at a cost ranging from $1.50-2.50/gallon depending on the feedstock used. Current research aims at optimizing the use of different feedstocks as substrates for the oleaginous microbe along with the corresponding downstream operations associated with each feedstock. However, the capability of the engineered oleaginous microbe to utilize glucose (in pure form or mixtures from cellulosic/hemicellulosic biomass hydrolysates), crude glycerol, ethanol, acetate, and butyrate as a carbon source has been established.

In the processing scheme depicted in FIG. 2b the "product of $CO_2$ fixation" is used for the growth of the oleaginous microbe and oil production. In some embodiments, this product is acetate. The reason to use acetate is two-fold: First, acetate is the product of most acetogens fixing anaerobically $CO_2$, hence there is significant prior knowledge on this topic, along with the genes and molecular constructs that are required to further modulate the acetogenic W-L pathway (FIG. 1). The second reason is that the oleaginous organism can readily metabolize acetate and produce TAG. FIG. 4 shows a time course for the growth of the oleaginous *Y. lipolytica* overexpressing SCD on 5% and 10% acetate. It can be seen that growth was uninhibited even at acetate levels of greater than 10%. The growth of the mutant was observed to be at least 3-fold greater than the parental strain. Oil production by the mutant was similarly 3-fold greater than that of the parental strain.

Example 2: Microbial Conversion of $H_2/CO_2$ to Acetate

Production of acetate from $H_2/CO_2$ proceeds through the Wood-Ljungdahl pathway. This metabolic pathway has been well-studied (71). Numerous groups have isolated various acetogens which can produce acetate (72-74). These acetogens produce acetate according to the following equation:

$$4H_2 + 2CO_2 \rightarrow CH_3COOH + 2H_2O \qquad (Eq.\ 3)$$

Figure 6:
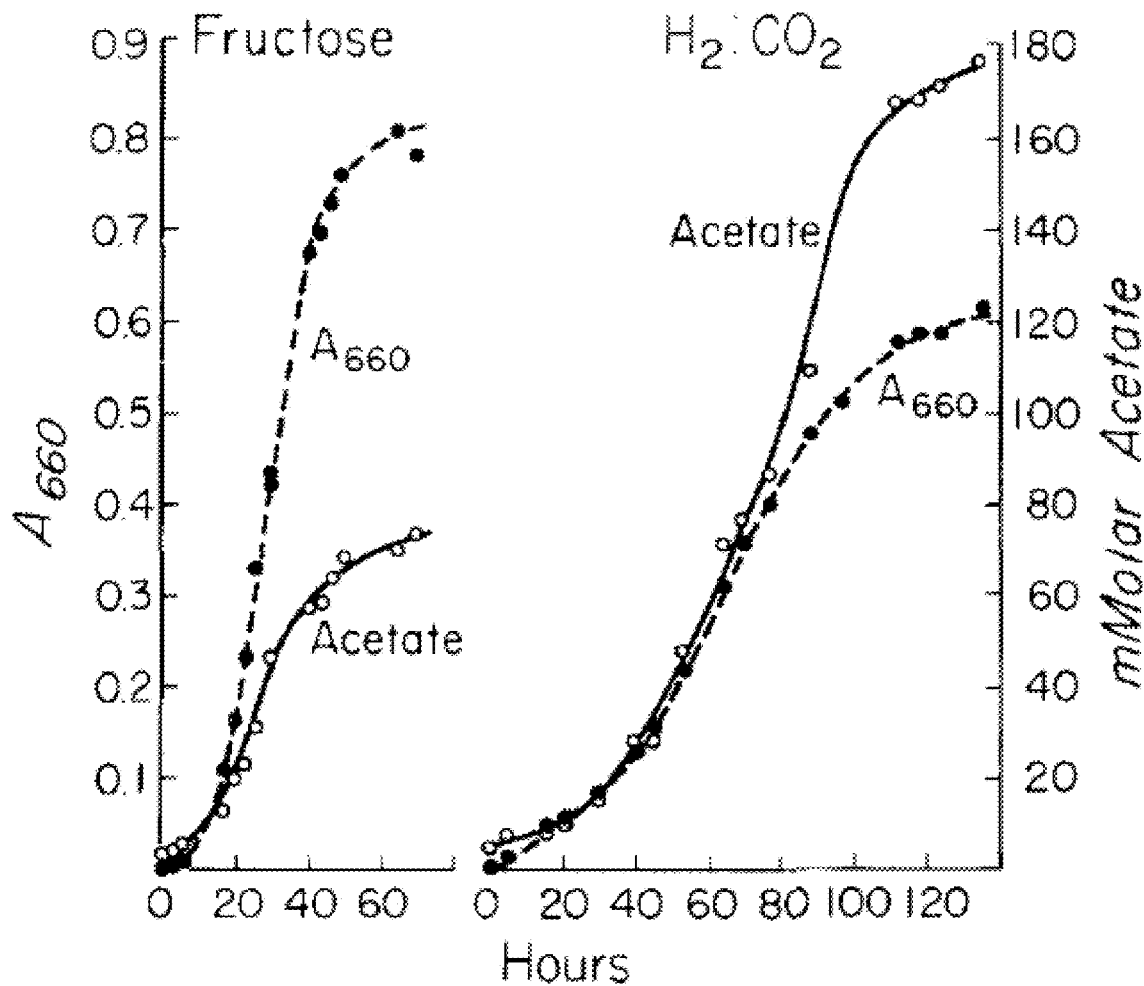
FIG. 6. Growth and acetate production of *Acetobacterium woodii* on fructose and $H_2/CO_2$. (71)

Most acetogens produce acetate at almost theoretical yields. While there has been much research in understanding the mechanisms behind this pathway, there has been very little research since the 1980's on improving the rate of acetate production by these organisms. As an example, FIG. 6 shows growth and acetate production characteristics of an acetogenic strain (*Acetobacterium woodii*) researched in the 1970's (72).

The mass yield of this stoichiometry is calculated to be 7.375 g acetate/g $H_2$. From the graph, an acetate productivity of approximately 2.5 g/L/day can be estimated. At this productivity and titer, it is estimated that 213 M gallons of liquid culture would be necessary to produce enough acetate to be processed into 50 million gallons of biodiesel per year (see Table 2). In a typical production plant, this would require 213, 1M-gallon fermentors, a 25-30-fold increase relatively to ethanol fermentation processes with comparable annual output. At this productivity, therefore, the process would be economically infeasible. However, one should note the exceptionally low cell densities of these fermentations, approximately 25-30 fold lower than the OD of typical ethanol fermentations routinely run with the acetogens described herein. This indicates that the specific rate of $CO_2$ fixation and acetate production by the anaerobic bacteria of FIG. 6 are comparable to those of another anaerobic process, ethanol fermentation. Therefore, it is very likely that the total volumetric productivity of acetate production by anaerobic acetogens can be significantly increased by following two strategies: (1) increasing the cell density of the anaerobic fermentor while maintaining the same specific productivity, and, (2) by increasing the specific $CO_2$ fixation rate and rate of acetogenesis through metabolic engineering aiming at increasing the W-L pathway flux.

TABLE 2

| Scale and Efficiency Calculations | | |
|---|---|---|
| Basis | | |
| Running Days | 300 | days/year |
| Production of biodiesel | 50,000,000 | gallons/year |
| | 189,250,000 | Liters/year |
| | 166,540,000 | kg biodiesel/year |
| | 555,133 | kg biodiesel/day |
| Calculations | | |
| Amount of acetate required [a] | 2,022,419 | kg acetate/day |
| Acetogen culture volume required | 1,011,209,418 | L |
| | 267,162,330 | gallons |
| Number of 1M Fermentors needed | 267 | Fermentors |
| Productivities | Yields [c] | Conversions |
| Acetogenesis (Acetate) | 0.28 g oil/g glucose | 3.785 Liters/gallon |
| 2.0 g/L/day [b] | 0.274 g oil/g acetate | 0.88 kg biodiesel/Liter |

TABLE 2-continued

Scale and Efficiency Calculations

|  |  | 143 MJ/kg $H_2$ |
|---|---|---|
|  |  | 42.2 MJ/kg biodiesel |
|  | Hydrogen-to-Oil Energy Efficiency |  |
| H2 to Acetate Conversion |  | 7.375 g acetate/g $H_2$[d] |
| Acetate to Oil Conversion |  | 0.274 g oil/g acetate [c] |
|  |  | 2.024 g oil/g $H_2$ |
| Energy Efficiency [e] |  | 59.74% |
| Total Overall Photon-to-Oil Efficiency |  | Reference |
| PEC Efficiency (Light to H2) | 12.0% | (76) |
| Total Overall Photon Efficiency [f] | 7.17% |  |
| PV Efficiency (Light to Electricity) | 25.0% | (77) |
| Electrolyzer Efficiency (Electricity to H2) | 67.0% | (78) |
| Total Overall Photon Efficiency [f] | 10.01% |  |

[a] Assuming complete transesterification of oil to biodiesel, and no losses in acetate separation
[b] Report of 10 g/L in 5 days (71)
[c] Theoretical yields based on stoichiometric calculations
[d] 4 $H_2$ + 2 $CO_2$ → $CH_3COOH$ + 2 $H_2O$ (13)
[e] Defined as (liquid fuel energy out)/(hydrogen energy in)
[f] Defined as (liquid fuel energy out )/(photon energy in)

For increasing the functional cell mass, since growing biomass from hydrogen is not the primary purpose of this process, cells can be grown to a high density using some easily metabolizable growth substrate (e.g., glucose), and then the cells can be used in stationary phase to continuously convert $CO_2$ and $H_2$ into acetate, thus addressing the problem of low titers dictating excessive culture volumes for adequate production. Methods for improving acetogenic $CO_2$ fixation by implementing or increasing flux through the W-L pathway in acetogens are described elsewhere herein. Both approaches result in increased acetate titers.

Example 3: Acetate to Oil Stoichiometric Calculations

The theoretical yield of de novo synthesis of triacylglyceride from acetate was estimated using a carbon chain pivot method (75). Intermediate metabolites (e.g. glucose, pyruvate, acetyl-CoA) are used as central carbon pivots in balance equations involving segments of metabolic pathways. In order to obtain the stoichiometry for an entire metabolic pathway, balance equations are combined such that the intermediate carbon pivots sum to zero. After summation, the remaining non-pivot metabolites are either inputs (negative) or outputs (positive) of the pathway. This method can account for energetics as well by including co-factors such as ATP, NADH, NADPH in the pivot table and constraining these to positive values. The calculation of the stoichiometry for the conversion of glucose into tripalmitin (representative lipid) uses seven balance equations, which eliminates pyruvate, acetyl-CoA, NADH and NADPH from the total balance, to produce the final stoichiometry (shown in Example 4). Acetate is converted into acetyl-CoA, which is the precursor for both fatty acid elongation and cellular respiration. NADPH is generated in the Transhydrogenase Cycle (76).

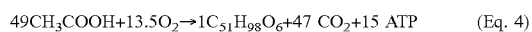

49$CH_3COOH$+13.5$O_2$→1$C_{51}H_{98}O_6$+47 $CO_2$+15 ATP     (Eq. 4)

It is observed that carbon flux is roughly split between anabolic and catabolic pathways, highlighting the energy intensive nature of lipid synthesis. On a mass basis, for 1 kg of tripalmitin produced, 3.64 kg of acetate is consumed and 2.5 kg of carbon dioxide is respired. This represents a theoretical mass yield of 0.274 g oil/g acetate. This is comparable to a calculated theoretical yield on glucose at 0.32 g oil/g glucose. The remaining hydrogen and oxygen (not shown in the equation) is in the form of water and reducing equivalents.

Example 4: Calculation of Overall Energy Efficiency

If it is assumed that hydrogen is the limiting factor, the yields of both bioprocesses (aerobic and anaerobic) can be combined and an overall yield for the process of producing oil from hydrogen can be obtained. On a mass basis the theoretical yield is 2.02 g oil/g $H_2$. This can be converted to an energy basis, according to the energy densities of biodiesel and hydrogen. The overall energy efficiency for our process, defined as energy content of fuel produced divided by energy content of hydrogen consumed, is 59.74% (see Table 2).

To facilitate comparison between other technologies, the biodiesel production scheme can be expanded to encompass processes for the production of hydrogen from sunlight. Two possible processes appear amenable: (1) direct hydrogen generation from sunlight via photo-electrochemical cells (PEC), (2) photovoltaic (PV) conversion of sunlight to electricity followed by the electrolysis of water to produce oxygen and hydrogen. PEC units can reach 12% efficiency under certain configurations (77). For PV, 40% efficiency is achievable, although 25% is much more common (78). Hydrolysis of water using an electrolyzer is estimated to have an energy efficiency of 67% (79). If we combine these efficiencies with the biodiesel production scheme, we obtain theoretical sunlight-to-biodiesel efficiencies of 7.17% for PEC and 10.01% for PV-hydrolysis (assuming 25% PV efficiency). PV-hydrolysis is the more efficient process. These theoretical efficiencies compare favorably to schemes dependent on photosynthesis that have efficiencies in the ranges of 0.1%-2% for plants and 2-6% for microalgae (80).

Example 5: Exemplary Process Flow Diagram

Figure 7:
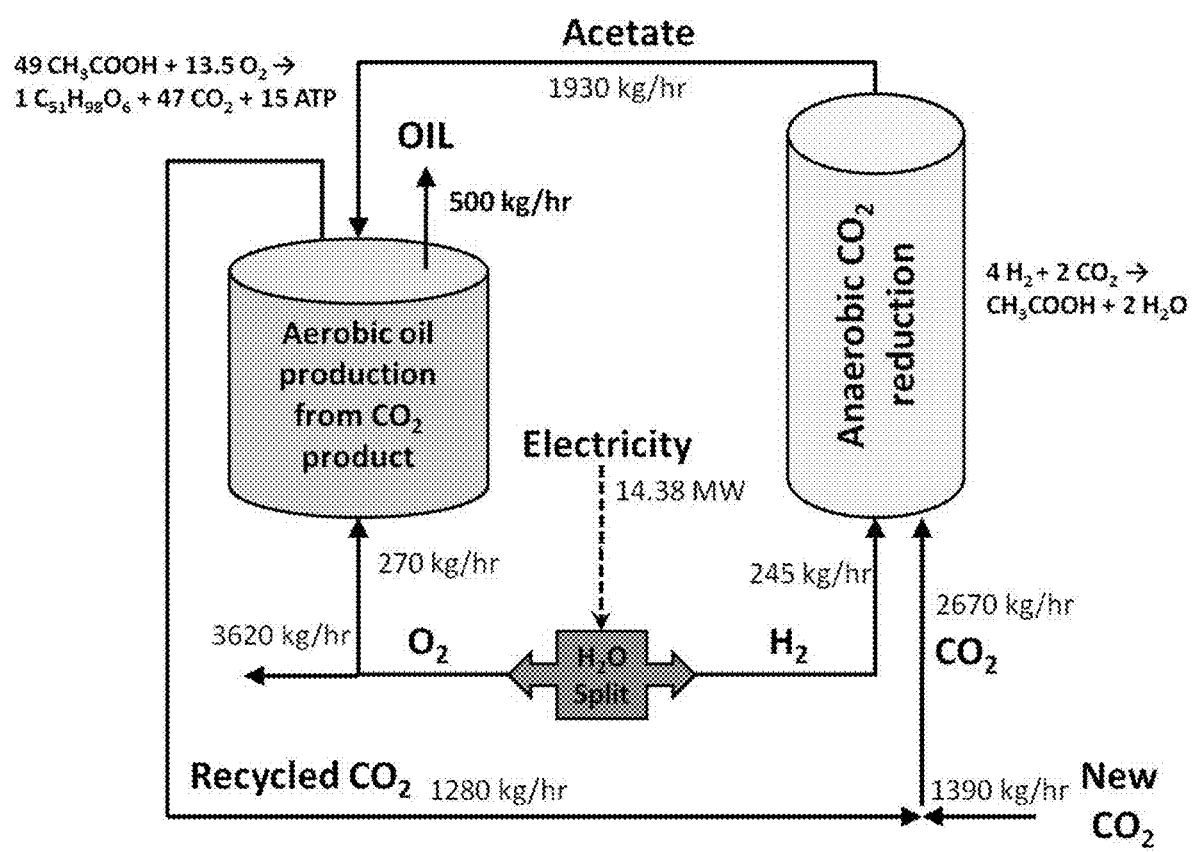
FIG. 7. Sample process flow diagram with basis of 500 kg/hr oil production (approx. 1M gallons/yr).

Possible flow rates can be estimated for implementation by incorporating the theoretical stochiometries into a process scheme, and performing a mass balance over the process (FIG. 7). A basis of 500 kg/hr oil production was used, which roughly translates into a small 1M gallon/yr oil production plant (note that water streams were omitted from the process diagram, and the stoichiometric equation for oil production from acetate also omits the production of water and reducing equivalents). The carbon dioxide recycled from the aerobic reactor contributes to half the total carbon dioxide demand in the anaerobic reactor. For the hydrolysis of water to form hydrogen and oxygen, an electric-to-hydrogen energy conversion efficiency of 67% (79) was used. Since there are only a few inputs to the process, the electricity consumed for electrolysis can give perspective to the level of power demand required for the process. 14.4 MW can reasonably be supplied by 3-4 wind turbines; a single wind turbine supplying about 3-5 MW each.

Example 6: Development of the Biocathode Screening Protocol and Construction of rMFC Recent studies (70) have shown that electrode potential significantly influences microbial community population dynamics, rates of EET and coulombic efficiency. Moreover, it was shown that active potentiostatic control of the electrodes can be used to select for (or possibly evolve) microbes with higher rates of EET and higher coulombic efficiencies (unpublished data), so active potentiostatic control is necessary to conduct robust, repeatable assessments of microbial bioelectrochemical activity.

In some embodiments, coupling of active potentiostatic measurement and control with a multi-well MFC (96 electrodes) is implemented to: a) screen for bioelectrical activity among strains, b) determine the electrode properties (e.g. potential, duty cycling) that are optimal for current production, and, c) identify strains with optimized current generation and coulombic efficiency. The 96-well MFC allows to ally substrate utilization with electron acceptance, end product production and microbial population growth. In concert with the electrochemical measurements, this approach provides the most comprehensive view of microbial metabolism (EET, metabolic rates) in relation to bioelectrochemical attributes.

Figure 5:
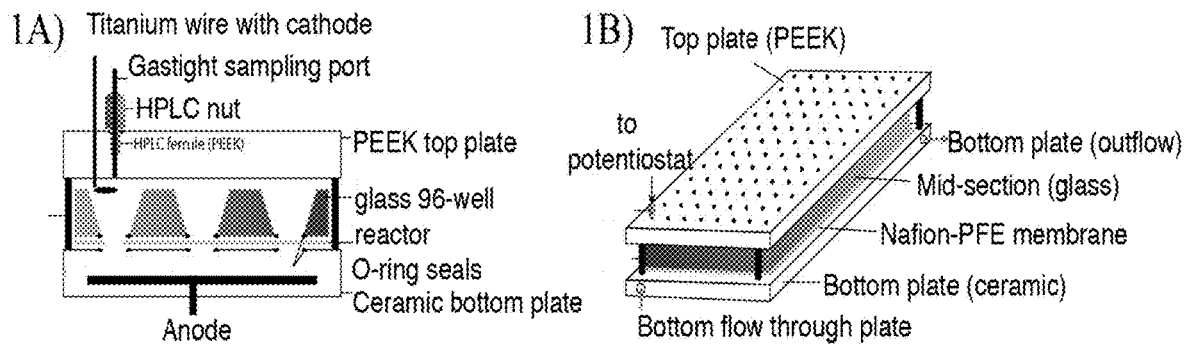
FIG. 5. Schematic of the 96-well MFC and experimental set-up. A) Cross-section of bioreactor showing components, including bottom plate electrode and flow path; B) Assembled reactor. A Gamry single-channel potentiostat and 12-channel multiplexer (not shown) are attached to the pins of the completed reactor below.

In some embodiments, the fermentors consist of three primary components, a top, a mid, and bottom plate (FIG. 5). In some embodiments, the top plate is fabricated of PEEK (chemically and biologically non-reactive) and milled to allow a "¼-28 thread" gastight HPLC fittings to be secured above each well of the glass plate. The fittings allow to sample fluids for microbial characterization, fluid characterization and dissolved gas analyses. In some embodiments, the top plate comprises a 1.5 mm hole to accommodate an insulated titanium wire. This wire can be potted in place and a small graphite electrode can be affixed to the wire using silver epoxy. This can serve as the cathode. In some embodiments, the mid-section of the bioreactor consists of a commercially available high strength glass 96-well microtitre plate (Rapp Polymer GmbH, Germany). These plates are available in several volumes (with different heights), from 1.5 µL to 1.5 mL. The appropriate size can be selected as needed. High-strength glass is ideal as it is cost-effective and electrically insulated. In some embodiments, the bottom plate of the bioreactor is fabricated of non-conductive machinable ceramic, and engineered to include a low gas permeability proton exchange membrane that physically separates each well (Nafion-PTFE 30%). The bottom plate can also include a flow-through channel that houses another larger electrode (about the length and width of the assembly). This electrode can be used for hydrolysis, and the subsequent hydrogen ions can diffuse across the membrane to support biosynthesis. The flow through channel can be flushed at a rate sufficient to insure steady state. Based on calculations, this bioreactor can be gastight and capable of withstanding 500 PSI (ca. 34atm) up to 110° C. This modular system represents the first bioreactor design that can be used to study aerobic or anaerobic microbial strains capable of EET, while keeping substrates and volatiles contained within the well, in a high-throughput format. In sum, this configuration will allow to a) interrogate up to 96 strains at a time, b) maintain each strain in well-defined conditions, c) poise each cathode independently by using a single-channel potentiostat and 12-channel multiplexer (Gamry Inc.), and d) ally microbial growth to electron acceptance and end product production.

In some embodiments, to screen for bioelectrical activity, select strains and mutants are placed into each well, in appropriate media and substrates. In some embodiments, strains will be run in quadruplicate for statistical robustness. In some embodiments, the gas headspace of each well is flushed with a $CO_2:N_2$ mix to achieve appropriate dissolved inorganic carbon concentrations and pH. When ready, the potentiostat is be configured to poise all 96 wells at a pre-determined potential. In some embodiments, experiments are run for up to 84 hours. This supports microbial growth within the wells and allows the establishment of active biofilms on the electrode. In some embodiments, upon completion of the cycle, a fluid and gas headspace sample is manually collected from each well and analyzed for changes in total inorganic carbon via gas chromatography and for end product production using, for example, a gas chromatograph outfitted to extract gasses from aqueous phases, and capable of quantifying carbon dioxide, oxygen, nitrogen, sulfide, methane, and carbon monoxide.

To be considered for further characterization, an isolate must: a) demonstrate bioelectrical activity; b) measurably reduce the inorganic carbon concentration in the well, c) produce a measurable quantity of the desired end product (acetate). In some embodiments, a strain satisfying these criteria is subjected to another round of testing. In some embodiments, each such strain is loaded into a total of 24 wells prepared as described above. To determine optimal potential for electron acceptance, potentiometry is used to identify the optimal potential for microbial electron acceptance for each strain. In some embodiments, to enable robust quantification of coulombic efficiency and to constrain reaction kinetics, each select strain is again be grown in 24 wells. Four wells are subject to the pre-determined potential for one hour. The multiplexer then subjects the next four wells to a different potential for two hours and so on, up to six hours at potential (this can be done sequentially, so that the total incubation time is 21 hours). These measurements (chrono-amperometry) provide a time-course of carbon reduction and biofuel production, enabling robust quantification of coulombic efficiency, as well as reaction kinetics. In some embodiments, media from each strain are also subjected to cyclic voltammetry to potentially identify any redox-active electron shuttles.

In some embodiments, the identified strains are further tested using a medium-scale reverse MFC (rMFC). For example, this reactor can be approximately two liters in volume, consisting of two glass reactors separated by a proton exchange membrane (White et al 2009; Reimers et al 2007). Briefly, the reactor embodies the same principles as above but also includes a distinct chamber for anode and cathode. The exemplary rMFC uses 24×1 cm diameter rods to form an electrode array. The rMFC can be inoculated with a target strain, and can be subjected to the same tests described in the higher resolution screening above. In addition, stable isotopically-labeled precursors (e.g., $^{13}C$ bicarbonate) can be used during the course of the incubations to trace the fate of inorganic carbon.

REFERENCES

1. Agrawal R S N, Ribeiro F H, Delgass W N. 2007. Sustainable fuel for the transportation sector. PNAS 104: 4828-33
2. El Abed M M, Marzouk B, Medhioub M N, Helal A N, Medhioub A. 2008. Microalgae: a potential source of polyunsaturated fatty acids. Nutr Health 19: 221-6
3. Li Q, Du W, Liu D. 2008. Perspectives of microbial oils for biodiesel production. Appl Microbiol Biotechnol 80: 749-56
4. Alvarez H M, Steinbuchel A. 2002. Triacylglycerols in prokaryotic microorganisms. Appl Microbiol Biotechnol 60: 367-76
5. Voss I, Steinbuchel A. 2001. High cell density cultivation of *Rhodococcus opacus* for lipid production at a pilot-plant scale. Appl Microbiol Biotechnol 55: 547-55
6. Lu X, Vora H, Khosla C. 2008. Overproduction of free fatty acids in *E. coli*: implications for biodiesel production. Metab Eng 10: 333-9
7. Steen E J, Kang Y, Bokinsky G, Hu Z, Schirmer A, McClure A, Del Cardayre S B, Keasling J D. 2010. Microbial production of fatty-acid-derived fuels and chemicals from plant biomass. Nature 463: 559-62
8. Beopoulos A, Cescut J, Haddouche R, Uribelarrea J L, Molina-Jouve C, Nicaud J M. 2009. *Yarrowia lipolytica* as a model for bio-oil production. Prog Lipid Res 48: 375-87
9. Papanikolaou S, Chevalot I, Komaitis M, Marc I, Aggelis G. 2002. Single cell oil production by *Yarrowia lipolytica* growing on an industrial derivative of animal fat in batch cultures. Appl Microbiol Biotechnol 58: 308-12
10. Gouveia L, Oliveira A C. 2009. Microalgae as a raw material for biofuels production. J Ind Microbiol Biotechnol 36: 269-74
11. Greenwell H C, Laurens L M, Shields R J, Lovitt R W, Flynn K J. 2009. Placing microalgae on the biofuels priority list: a review of the technological challenges. J R Soc Interface
12. Raymond J. 2005. The Evolution of Biological Carbon and Nitrogen Cycling—a Genomic Perspective. Reviews in Mineralogy and Geochemistry 59: 211-31
13. Drake H L, Goessner A S, Daniel S L. 2008. Old acetogens, new light. Annals of the New York Academy of Sciences 1125: 100-28
14. Muller V. 2003. Energy Conservation in Acetogenic Bacteria. Appl. Environ. Microbiol. 69: 6345-53
15. Verser D, Eggeman T. 2003. U.S. Pat. No. 6,509,180
16. Muller V, Imkamp F, Biegel E, Schmidt S, Dilling S. 2008. Discovery of a Ferredoxin: NAD(+)-Oxidoreductase (Rnf) in *Acetobacterium woodii*—A novel potential coupling site in acetogens. Incredible Anaerobes: from Physiology to Genomics to Fuels 1125: 137-46
17. Ragsdale S W. 2008. Enzymology of the Wood-Ljungdahl pathway of acetogenesis
18. Paredes C J, Alsaker K, Papoutsakis E T. 2005. A comparative genomic view of clostridial sporulation and physiology. Nature Reviews Microbiology 3: 969-78
19. Ezeji T C, Qureshi N, Blaschek H P. 2007. Bioproduction of butanol from biomass: from genes to bioreactors. Current Opinion in Biotechnology 18: 220-7
20. Gheshlaghi R S J, Moo-Young M, Chou C P. 2009. Metabolic pathways of clostridia for producing butanol. Biotechnol Adv 27: 764-81
21. Papoutsakis E T. 2008. Engineering solventogenic clostridia. Current Opinion in Biotechnology 19: 420-9
22. Sillers R, Chow A, Tracy B, Papoutsakis E T. 2008. Metabolic engineering of the non-sporulating, non-solventogenic *Clostridium acetobutylicum* strain M5 to produce butanol without acetone demonstrate the robustness of the acid-formation pathways and the importance of the electron balance. Metab Eng 10: 321-32
23. Sillers R, Al-Hinai M A, Papoutsakis E T. 2009. Aldehyde-alcohol dehydrogenase and/or thiolase overexpression coupled with CoA transferase downregulation lead to higher alcohol titers and selectivity in *Clostridium acetobutylicum* fermentations. Biotechnol Bioeng 102: 38-49
24. He Z, Angenent L T. 2006. Application of bacterial biocathodes in microbial fuel cells. Electroanalysis 18: 2009-15
25. Reimers C, Girguis, P. R., Stecher, H., Tender, L., Ryckelynck, N., and Whaling, P. 2006. Microbial fuel cell energy from an ocean cold seep. Geobiology 4: 123-36
26. Clauwaert P, Van der Ha D, Boon N, Verbeken K, Verhaege M, Rabaey K, Verstraete W. 2007. Open air biocathode enables effective electricity generation with microbial fuel cells. Environmental Science & Technology 41: 7564-9
27. Rabaey K, Read S T, Clauwaert P, Freguia S, Bond P L, Blackall L L, Keller J. 2008. Cathodic oxygen reduction catalyzed by bacteria in microbial fuel cells. Isme Journal 2: 519-27
28. Van Rijn J, Tal Y, Schreier H J. 2006. Denitrification in recirculating systems: Theory and applications. Aquacultural Engineering 34: 364-76
29. Lewis K. 1966. Symposium on Bioelectrochemistry of Microorganisms 0.4. Biochemical Fuel Cells. Bacteriological Reviews 30: 101-&
30. Gregory K B, Bond D R, Lovley D R. 2004. Graphite electrodes as electron donors for anaerobic respiration. Environmental Microbiology 6: 596-604
31. Clauwaert P, Rabaey K, Aelterman P, De Schamphelaire L, Ham T H, Boeckx P, Boon N, Verstraete W. 2007. Biological denitrification in microbial fuel cells. Environmental Science & Technology 41: 3354-60
32. Thrash J C, Van Trump J I, Weber K A, Miller E, Achenbach L A, Coates J D. 2007. Electrochemical stimulation of microbial perchlorate reduction. Environmental Science & Technology 41: 1740-6
33. Shea C, Clauwaert P, Verstraete W, Nerenberg R. 2008. Adapting a denitrifying biocathode for perchlorate reduction. Water Sci Technol 58: 1941-6
34. Rozendal R A, Jeremiasse A W, Hamelers H V, Buisman C J. 2008. Hydrogen production with a microbial biocathode. Environ Sci Technol 42: 629-34
35. Cheng S, Xing D, Call D F, Logan B E. 2009. Direct biological conversion of electrical current into methane by electromethanogenesis. Environ Sci Technol 43: 3953-8
36. Clauwaert P. 2010. Bioelectrochemical reductions in reactor systems. In Bioelectrochemical Systems, ed. K Rabaey, L Angenent, U Schroder, J Keller, pp. 285-304. London: IWA Publishing Alliance House
37. Strycharz S M, Woodard T L, Johnson J P, Nevin K P, Sanford R A, Loffler F E, Lovley D R. 2008. Graphite electrode as a sole electron donor for reductive dechlorination of tetrachlorethene by *Geobacter lovleyi*. Applied and Environmental Microbiology 74: 5943-7

38. Gregory K B, Lovley D R. 2005. Remediation and recovery of uranium from contaminated subsurface environments with electrodes. Environmental Science & Technology 39: 8943-7

39. Rabaey K. 2010. Bioelectrochemical systems: A new approach towards environmental and industrial biotechnology. In Bioelectrochemical Systems: From Extracellular Electron Transfer to Biotechnological Application, ed. K Rabaey, L Angenent, U Schroder, J Keller, pp. 1-16. London: IWA Publishing 40. Debabov V G. 2008. Electricity from microorganisms. Microbiology 77: 123-31

41. Logan B, Grot S, Mallouk T, Liu H. 2009. United States

42. Hongo M, Iwahara M. 1979. Electrochemical studies on fermentation 1. Application of electro-energizing method to 1-glutamic acid fermentation. Agricultural and Biological Chemistry 43: 2075-81

43. Emde R, Schink B. 1990. Enhanced propionate formation by *Propionibacterium freudenreichii* subsp *freudenreichii* in a 3-electrode amperometric culture system. Applied and Environmental Microbiology 56: 2771-6

44. Park D H, Zeikus J G. 1999. Utilization of electrically reduced neutral red by *Actinobacillus succinogenes*: Physiological function of neutral red in membrane-driven fumarate reduction and energy conservation. Journal of Bacteriology 181: 2403-10

45. Rabaey K, Van de Sompel K, Maignien L, Boon N, Aelterman P, Clauwaert P, De Schamphelaire L, Pham H T, Vermeulen J, Verhaege M, Lens P, Verstraete W. 2006. Microbial fuel cells for sulfide removal. Environmental Science & Technology 40: 5218-24

46. Clauwaert P, Toledo R, Van der Ha D, Crab R, Verstraete W, Hu H, Udert K M, Rabaey K. 2008. Combining biocatalyzed electrolysis with anaerobic digestion. Water Science and Technology 57: 575-9

47. Reda T, Plugge C M, Abram N J, Hirst J. 2008. Reversible interconversion of carbon dioxide and formate by an electroactive enzyme. Proceedings of the National Academy of Sciences of the United States of America 105: 10654-8

48. Steinbusch K, Hamelers H V M, Buisman C J N. 2008. Alcohol production through volatile fatty acids reduction with hydrogen as electron donor by mixed cultures. Water Research 42: 4059-66

49. Harris L M, Blank L, Desai R P, Welker N E, Papoutsakis E T. 2001. Fermentation characterization and flux analysis of recombinant strains of *Clostridium acetobutylicum* with an inactivated solR gene. Journal of Industrial Microbiology & Biotechnology 27: 322-8

50. Harris L M, Desai R P, Welker N E, Papoutsakis E T. 2000. Characterization of recombinant strains of the *Clostridium acetobutylicum* butyrate kinase inactivation mutant: Need for new phenomenological models for solventogenesis and butanol inhibition? Biotechnology and Bioengineering 67: 1-11

51. Hillmann F, Fischer R J, Saint-Prix F, Girbal L, Bahl H. 2008. PerR acts as a switch for oxygen tolerance in the strict anaerobe *Clostridium acetobutylicum*. Molecular Microbiology 68: 848-60

52. Tracy B P, Paredes C J, Papoutsakis E T. 2009. Methods and composition for generating sporulation deficient bacteria. U.S. patent application Ser. No. 12/485,636 (Jun. 16, 2009).

53. Cornillot E, Nair R V, Papoutsakis E T, Soucaille P. 1997. The genes for butanol and acetone formation in *Clostridium acetobutylicum* ATCC 824 reside on a large plasmid whose loss leads to degeneration of the strain. J Bacteriol 179: 5442-7

54. Jones S W, Paredes C J, Tracy B, Cheng N, Sillers R, Senger R S, Papoutsakis E T. 2008. The transcriptional program underlying the physiology of clostridial sporulation. Genome Biol 9: R114

55. Mermelstein L D, Welker N E, Bennett G N, Papoutsakis E T. 1992. Expression of Cloned Homologous Fermentative Genes in *Clostridium-Acetobutylicum* Atcc 824. Bio-Technology 10: 190-5

56. Lee S Y, Mermelstein L D, Bennett G N, Papoutsakis E T. 1992. Vector Construction, Transformation, and Gene Amplification in *Clostridium-Acetobutylicum* Atcc-824. Annals of the New York Academy of Sciences 665: 39-51

57. Tummala S B, Welker N E, Papoutsakis E T. 1999. Development and characterization of a gene expression reporter system for *Clostridium acetobutylicum* ATCC 824. Applied and Environmental Microbiology 65: 3793-9

58. Tomas C A, Alsaker K V, Bonarius HPJ, Hendriksen W T, Yang H, Beamish J A, Paredes C J, Papoutsakis E T. 2003. DNA array-based transcriptional analysis of asporogenous, nonsolventogenic *Clostridium acetobutylicum* strains SKO1 and M5. Journal of Bacteriology 185: 4539-47

59. Miller T L, Wolin M J. 1974. A serum bottle modification of the Hungate technique for cultivating obligate anaerobes. Appl Microbiol 27: 985-7

60. Monot F, Martin J R, Petitdemange H, Gay R. 1982. Acetone and Butanol Production by *Clostridium-Acetobutylicum* in a Synthetic Medium. Applied and Environmental Microbiology 44: 1318-24

61. Sakai S, Nakashimada Y, Yoshimoto H, Watanabe S, Okada H, Nishio N. 2004. Ethanol production from $H_2$ and $CO_2$ by a newly isolated thermophilic *bacterium, Moorella* sp. HUC22-1. Biotechnol Lett 26: 1607-12

62. Sakai S, Nakashimada Y, Inokuma K, Kita M, Okada H, Nishio N. 2005. Acetate and ethanol production from $H_2$ and $CO_2$ by *Moorella* sp. using a repeated batch culture. Journal of Bioscience and Bioengineering 99: 252-8

63. McLaughlin J K, Meyer C L, Papoutsakis E T. 1985. Gas chromatography and gateway sensors for on-line state estimation of complex fermentations (butanol-acetone fermentation). Biotechnol Bioeng 27: 1246-57

64. Wood H G. 1952. A study of carbon dioxide fixation by mass determination of the types of C13-acetate. J Biol Chem 194: 905-31

65. StimHerndon K P, Nair R, Papoutsakis E T, Bennett G N. 1996. Analysis of degenerate variants of *Clostridium acetobutylicum* ATCC 824. Anaerobe 2: 11-8

66. Bertram J, Stratz M, Dune P. 1991. Natural transfer of conjugative transposon Tn916 between gram-positive and gram-negative bacteria. Journal of Bacteriology 173: 443-8

67. Sass C, Walter J, Bennett G N. 1993. Isolation of mutants of *Clostridium acetobutylicum* ATCC 824 deficient in protease activity. Current Microbiology 26: 151-4

68. Young D I, Evans V J, Jefferies J R, Jennert K C B, Phillips ZEV, Ravagnani A, Young M. 1999. Genetic methods in clostridia. In Methods Microbiology, Vol 29, pp. 191-207. San Diego: Academic Press Inc 69. Papoutsakis E T, Tracy B P. Patent No. WO2009137778-A2

70. White H K R C, Cordes E E, Dilly G F, Girguis P R. 2009. Quantitative population dynamics of microbial communities in plankton-fed microbial fuel cells. ISME J. 3: 635-46
71. Ragsdale S W, Wood H G. 1991. Enzymology of the acetyl-CoA pathway of $CO_2$ fixation. Critical reviews in biochemistry and molecular biology 26: 261-300
72. Balch W E, Schoberth S, Tanner R S, Wolfe R S. 1977. *Acetobacterium*, a new genus of hydrogen-oxidizing, carbon dioxide-reducing, anaerobic bacteria. International Journal of Systematic and Evolutionary Microbiology 27: 355
73. Kane M D, Brauman A, Breznak J A. 1991. *Clostridium mayombei* sp. nov., an H 2/CO2 acetogenic *bacterium* from the gut of the African soil-feeding termite, *Cubitermes speciosus*. Archives of Microbiology 156: 99-104
74. Schulman M, Ghambeer R K, Ljungdahl L G, Wood H G. 1973. Total synthesis of acetate from $CO_2$. VII. Evidence with *Clostridium thermoaceticum* that the carboxyl of acetate is derived from the carboxyl of pyruvate by transcarboxylation and not by fixation of CO2. Journal of Biological Chemistry 248: 6255
75. van Milgen J. 2002. Modeling Biochemical Aspects of Energy Metabolism in Mammals. J. Nutr. 132: 3195-202
76. Ratledge C. 2004. Fatty acid biosynthesis in microorganisms being used for Single Cell Oil production. Biochimie 86: 807-15
77. Bak T, Nowotny J, Rekas M, Sorrell C C. 2002. Photo-electrochemical hydrogen generation from water using solar energy. Materials-related aspects. International Journal of Hydrogen Energy 27: 991-1022
78. Green M A, Emery K, Hishikawa Y, Warta W. 2009. Solar cell efficiency tables (version 33). Progress in Photovoltaics: Research and Applications 17: 85-94
79. Kroposki B, Sen P K, Harrison K, Levene J, Novachek F. 2006. Electrolysis:
Information and opportunities for electric power utilities: United States. Dept. of Energy
80. Weyer K M, Bush D R, Darzins A, Willson B D. 2009. Theoretical Maximum Algal Oil Production. BioEnergy Research: 1-10

All publications, patents and sequence database entries mentioned herein, including those items listed below, are hereby incorporated by reference for the teachings referenced herein as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Articles such as "a," "an," and "the," as used herein, may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process.

The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim or another portion of the description. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

The invention claimed is:

1. A method comprising
   (a) culturing in a liquid medium a first organism in the presence of a carbon source under aerobic conditions suitable for the first organism to oxidize the carbon source, wherein the conditions are oxidizing conditions, wherein the first organism produces $CO_2$ as part of the oxidation process; and
   (b) culturing in a liquid medium a second organism in the presence of $CO_2$ produced in (a) under anaerobic conditions suitable for the second organism to reduce the $CO_2$, wherein the conditions are reducing conditions, wherein the second organism produces a carbon substrate as part of the reduction process;
      wherein the culturing of (a) and of (b) is carried out in separate fermenters; and
      wherein the carbon substrate produced in (b) is used as a carbon source by the organism of (a).

2. The method of claim 1, further comprising contacting the first organism with an oxidizing agent, optionally wherein the oxidizing agent is $O_2$.

3. The method of claim 1, further comprising contacting the second organism with a reducing agent, optionally wherein the reducing agent is $H_2$, CO, syngas, or $H_2S$.

4. The method of claim 1, further comprising providing electrons to the second organism of (b) by contacting the second organism of (b) with an electric current.

5. The method of claim 1, wherein the carbon source is a carbohydrate, optionally glucose, fructose, ethanol, butyrate, butanol, acetate, acetic acid, biomass, cellulose, or hemicellulose.

6. The method of claim 1, wherein the product of the carbon source oxidization process in (a) is a lipid, optionally an edible lipid, or a precursor thereof.

7. The method of claim 1, wherein the carbon substrate produced in (b) is a biofuel or ethanol.

8. The method of claim 1, wherein the organism of (a) is an oleaginous yeast, optionally *Y. lipolytica*.

9. The method of claim 1, wherein the organism of (b) is an acetogenic *bacterium*, optionally a *Clostridium* sp. *bacterium, C. acetobutylicum, C. ljungdahlii, C. carboxydivorans*, or *C. autoethanogenum, C. thermohydrosulfuricum, C. thermocellum*, or *C. thermoanaerofacter ethanoliticus*.

10. The method of claim 1, wherein the organism of (a) and/or (b) is genetically modified, optionally wherein the organism of (a) overexpresses a stearoyl-CoA desaturase gene.

11. A method of producing lipids comprising:
   providing $CO_2$ to a first organism in an anaerobic fermentor, wherein the first organism converts the $CO_2$ to a carbon substrate;
   removing the carbon substrate from the anaerobic fermentor; and
   providing the carbon substrate to a second organism in an aerobic fermentor, wherein the second organism converts the carbon substrate to a lipid or a precursor thereof and $CO_2$;
   wherein the anaerobic fermentor and the aerobic fermentor are separate fermentors.

12. The method of claim 11, further comprising
   removing the $CO_2$ from the aerobic fermentor; and
   providing the $CO_2$ to the first organism in the anaerobic fermentor.

13. The method of claim 11, wherein the first organism is a $CO_2$-fixing *bacterium*, optionally a *Clostridium* sp. *bacterium, C. acetobutylicum, C. ljungdahlii, C. carboxydivorans, C. autoethanogenum, C. thermohydrosulfuricum, C. thermocellum*, or *C. thermoanaerofacter ethanoliticus*.

14. The method of claim 11, wherein the second organism is an oleaginous yeast, optionally *Y. lipolytica*.

15. The method of claim 11, wherein the first and/or second organisms are genetically modified.

16. The method of claim 11, wherein the carbon substrate is ethanol, butyrate, butanol, acetate, or acetic acid.

17. The method of claim 11, wherein the anaerobic fermentor comprises a reducing agent, optionally $H_2$, CO, syngas, or $H_2S$.

18. The method of claim 11, further comprising providing electrons to the first organism by contacting the first organism with an electrical current, optionally wherein the electrical current is provided by at least one electrode.

* * * * *